United States Patent [19]

Thornes et al.

[11] Patent Number: 5,525,626

[45] Date of Patent: Jun. 11, 1996

[54] TREATING SUSCEPTIBLE HUMAN MALIGNANT TUMORS WITH 7-HYDROXY-1,2-BENZOPYRONE

[75] Inventors: Douglas R. Thornes, Dublin, Ireland; Helga Stolze, Göttingen, Germany; Ernest Marshall, Cincinnati, Ohio; Kurt Zänker, München, Germany; Manly E. Marshall, Cincinnati, Ohio

[73] Assignee: Schaper & Bruemmer GmbH & Co., Germany

[21] Appl. No.: 334,376

[22] Filed: Nov. 3, 1994

Related U.S. Application Data

[63] Continuation of Ser. No. 743,314, Aug. 16, 1991, abandoned.

[30] Foreign Application Priority Data

Nov. 24, 1989 [DE] Germany ............... 39 38 902.2

[51] Int. Cl.$^6$ ............... A61K 31/35; A61K 31/56; A61K 31/505; A61K 33/24
[52] U.S. Cl. ............... 514/457; 514/171; 514/274; 424/649
[58] Field of Search ............... 514/457, 171

[56] References Cited

PUBLICATIONS

*Plantica Medica*, vol 53 (6), (1987), pp. 526–529, "Cytostatic Activity of Coumarins in vitro," Gawron, et al.
*Chemical Abstracts*, vol. 99, No. 1, Jul. 4, 1983, Columbus, Ohio, p. 301, "Plant anticancer agents, XXVI, Constituents of Peddica fischeri," Handa et al.
*Chemical Abstracts*, vol. 105, No. 25, Dec. 22, 1986, Columbus, Ohio, pp. 448–449, "Plant anticancer agents, XLII, Cytotoxic constituents from Wikstroemia elliptica," Duh et al.
*Pharmazie*, vol. 36, H.2 (1981), p. 166, "Preparation and Antitumour Property of Certain Coumarins and Psoralens," Loutfy.
*Cancer Research*, vol. 39, May 1979, Minneapolis, Minnesota, pp. 1651–1654, "Inhibition of Chemical Carcinogen-–Induced Neoplasia by Coumarins and α-Angelicalactone," Wattenberg et al.
*Journal of the National Cancer Institute*, vol. 56, No. 6, Jun. 1976, pp. 1237–1242, "Cocarcinogenic and Tumor–Promoting Agents in Tobacco Carcinogenesis," Van Duuren et al.
*J. Neurosurg*, vol. 71, Oct. 1989, pp. 551–557, Chicago, Illinois, "Effect of nordihydroguaiaretic acid on cultured rat and human glioma cell proliferation," Wilson et al.
*Chemical Abstracts*, vol 104, No. 9, Mar. 1986, p. 28, Columbus, Ohio, "Lipoxygenase inhibition and tumor promotor inhibition by medicinal plant components," Kato et al.
"A New Model System For Mammalian Mechanisms Of Anticarcinogenesis (Meeting Abstract)," Joenje et al., International Conference on Mechanisms of Antimutagenesis and Anticarcinogenesis, Oct. 6–10, 1985, Lawrence, Kansas Abstract only.
"Human Papilloma Virus Type 18 Sequence In Hela–Variants And Hela–Infected Established Cell Lines (Meeting Abstract)," Tong et al., Proc Annu Meet Am Assoc Cancer Res; 1991, Pittsburgh Pennsylvania Abstract only.
Journal Of Natural Products, 46, pp. 248–250, 1983, Chicago, Illinois, "Plant Anticancer Agents, XXVI, Constituents of Peddica Fischeri," Handa et al.
*Protocols for Screening Chemical Agents and Natural Products Against Animal Tumors and Other Biological Systems*, (Third Edition), 1972, Bethesda, Maryland, p. 9, Geran et al.
*Cancer Research*, vol. 48 (20) 1988, pp. 5660–2, van Helden et al "Cross Contamination of Human Esophageal Detected by DN Fingerprint Analysis" Abstract only.

*Primary Examiner*—Jerome D. Goldberg
*Attorney, Agent, or Firm*—Nixon & Vanderhye

[57] ABSTRACT

The invention relates to the use of 1,2-benzopyrone derivatives for the treatment of susceptible malignant tumors in human beings. The derivatives used according to the invention are suitable for both preventive and also therapeutic treatment and they display in particular growth-inhibiting effect vis-à-vis brain-tumor cells and cells from human renal, prostate, skin or lung carcinomas.

6 Claims, 23 Drawing Sheets

INFLUENCE OF 7-HYDROXY-1, 2-BENZOPYRONE ON MCF 7

□ 7-HYDROXY-1, 2-BENZOPYRONE
● CONTROL

IL 1 - SECRETION AFTER STIMULATION WITH 7-HYDROXY-1, 2-BENZOPYRONE

IL 6 - SECRETION AFTER STIMULATION WITH 7-HYDROXY-1, 2-BENZOPYRONE

COSTIMULATION OF TNF AND IL 1 OR IL 6
BY 7-OH-1, 2-BP
IN COMBINATION WITH ENDOTOXINES
SI = STIMULATION INDEX mRNA-DETERMINATION

COMBINATION OF 7-OH-1, 2-BP WITH TESTOSTERON

Fig. 10
DUKX- Cells
a: without 7-OH-1,2-BP     b: with 7-OH-1,2-BP
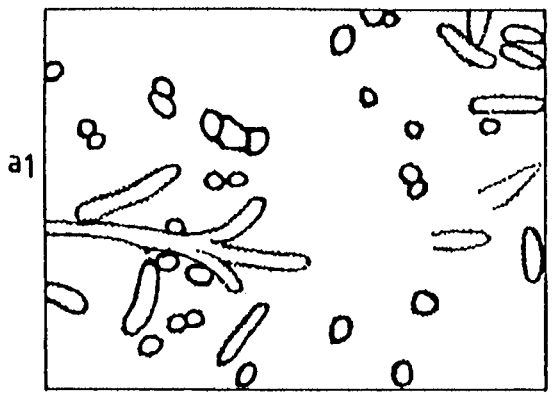
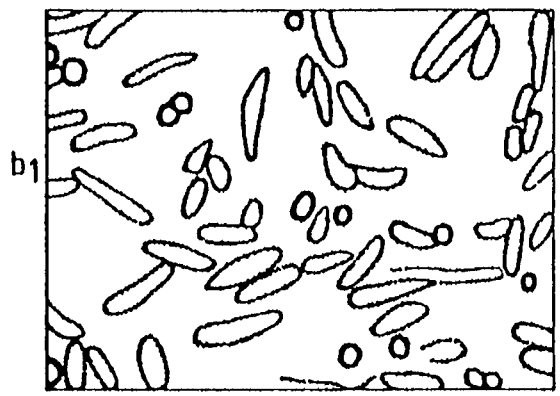
freshly inoculated cells after 24 hours
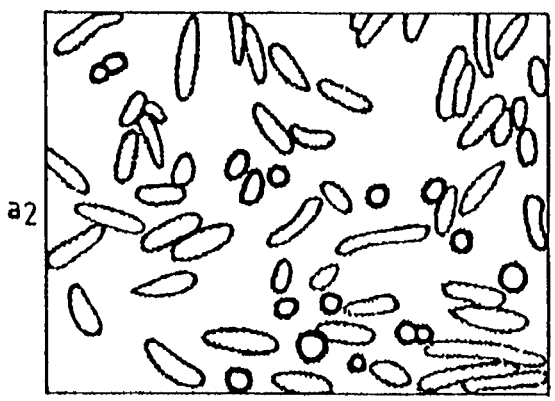
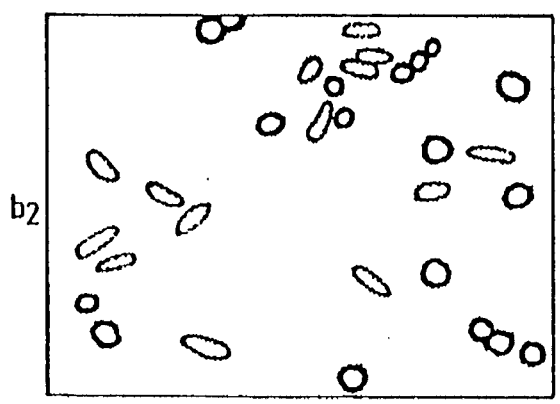
after 48 hours
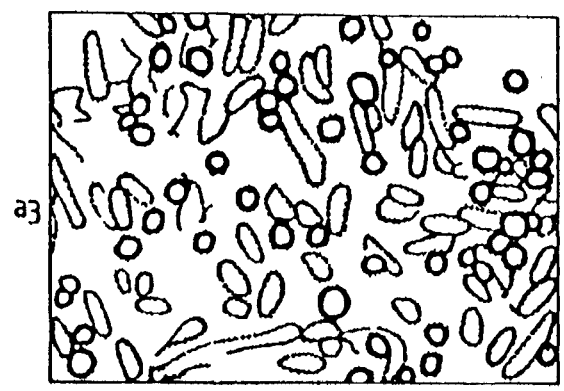
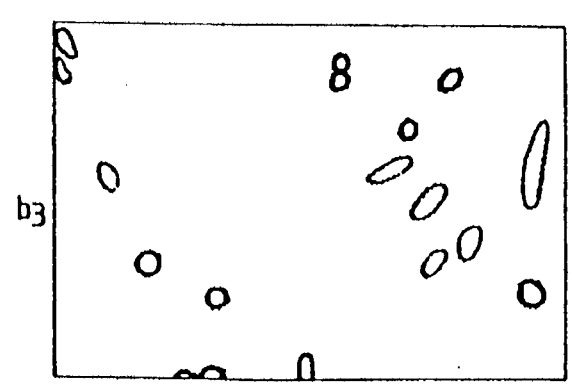
after 72 hours

Fig. 11

DUKX-Cells a: without 7-OH-1,2-BP

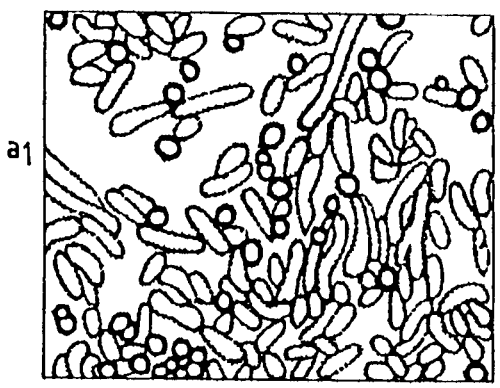

freshly inoculated cells after 72 hours

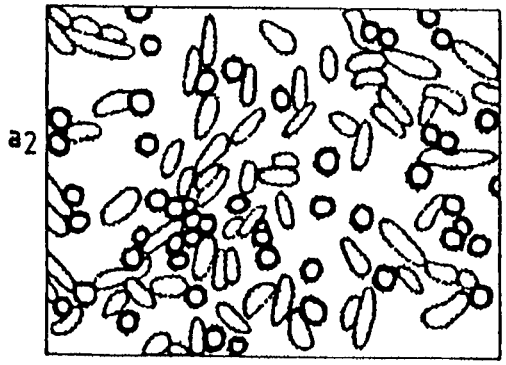

freshly inoculated cells after 72 hours b: with 7-OH-1,2-BP

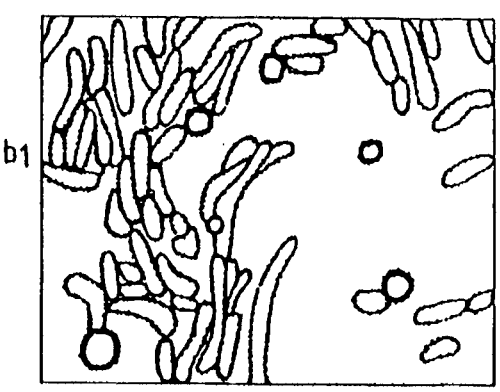

Cells 24 hours in the presence of 7-OH-1,2-BP, thereafter freed from active agent, trypsin-treated, fresh inoculated and 48 hours without 7-OH-1,2-BP.

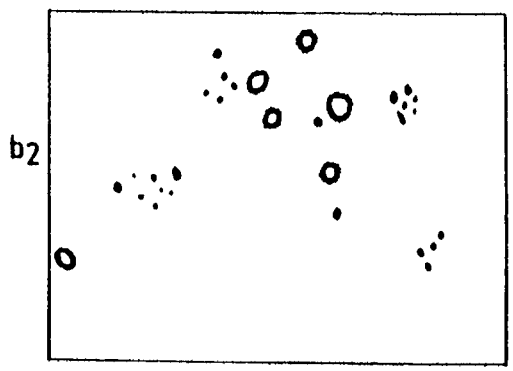

Cells 24 hours in the presence of 7-OH-1,2-BP, thereafter freed from active agent, trypsin-treated, freshly inoculated and 48 hours in the presence of 7-OH-1,2-BP.

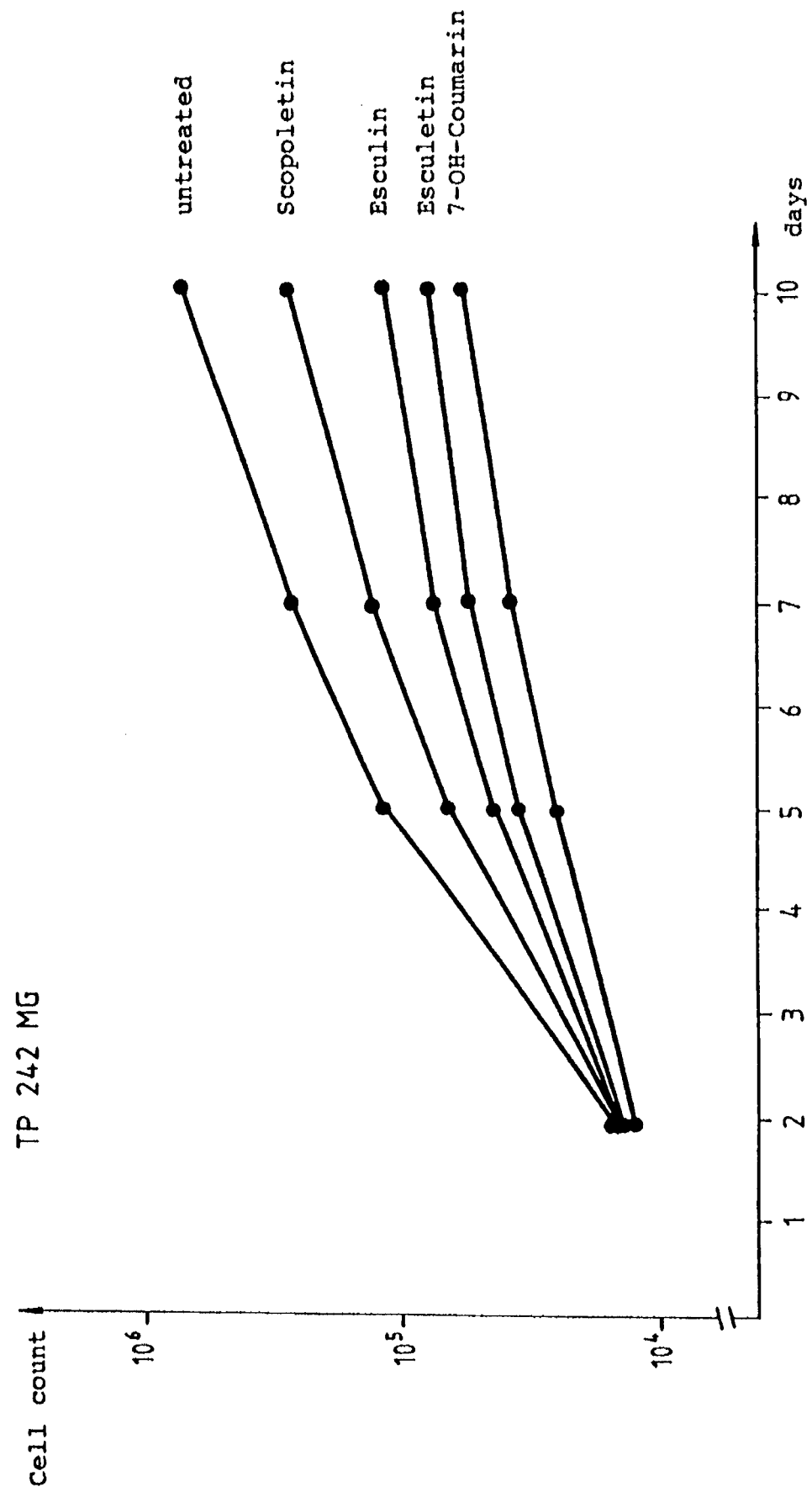
Fig.12 TP 242 MG

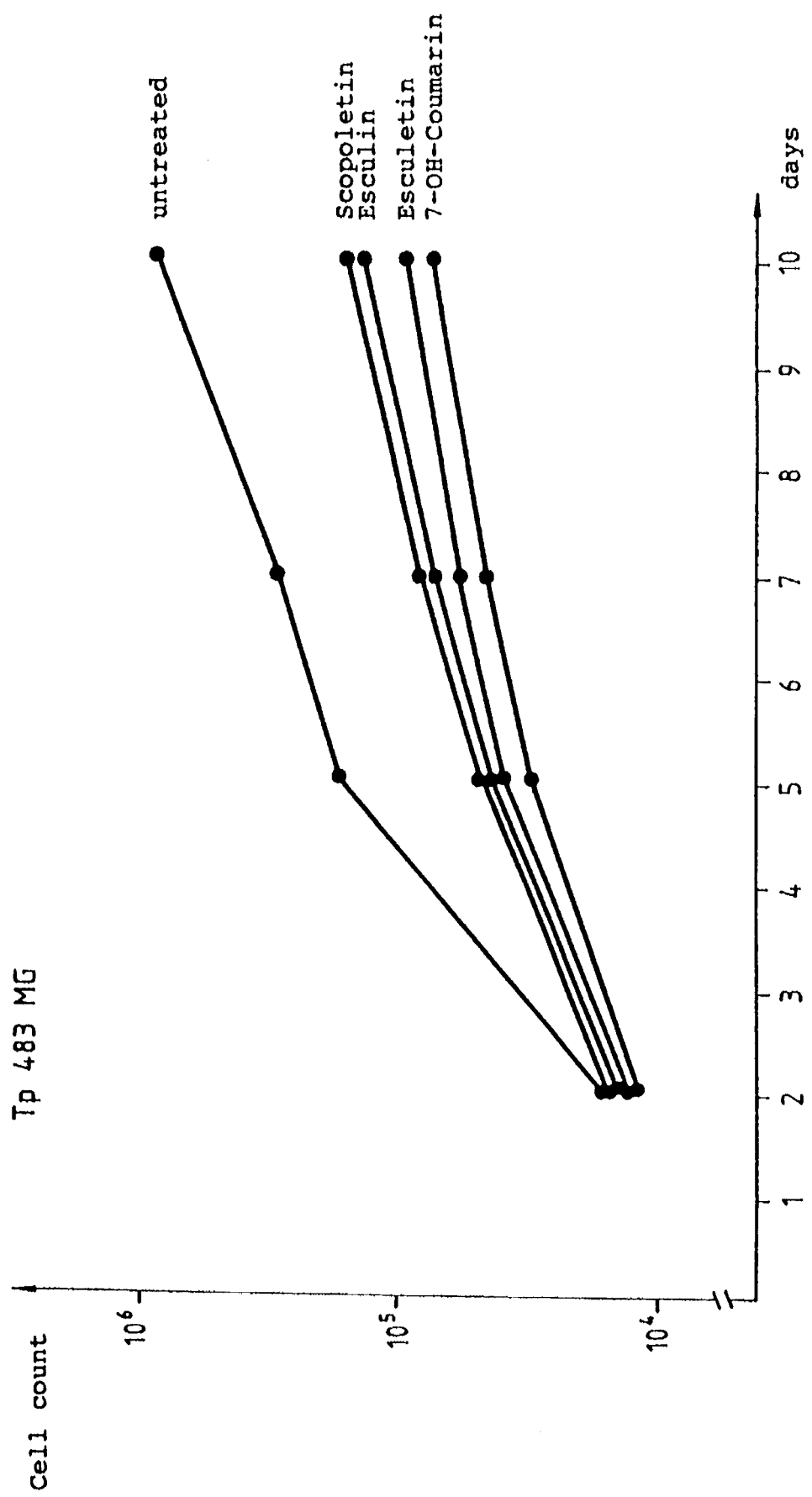

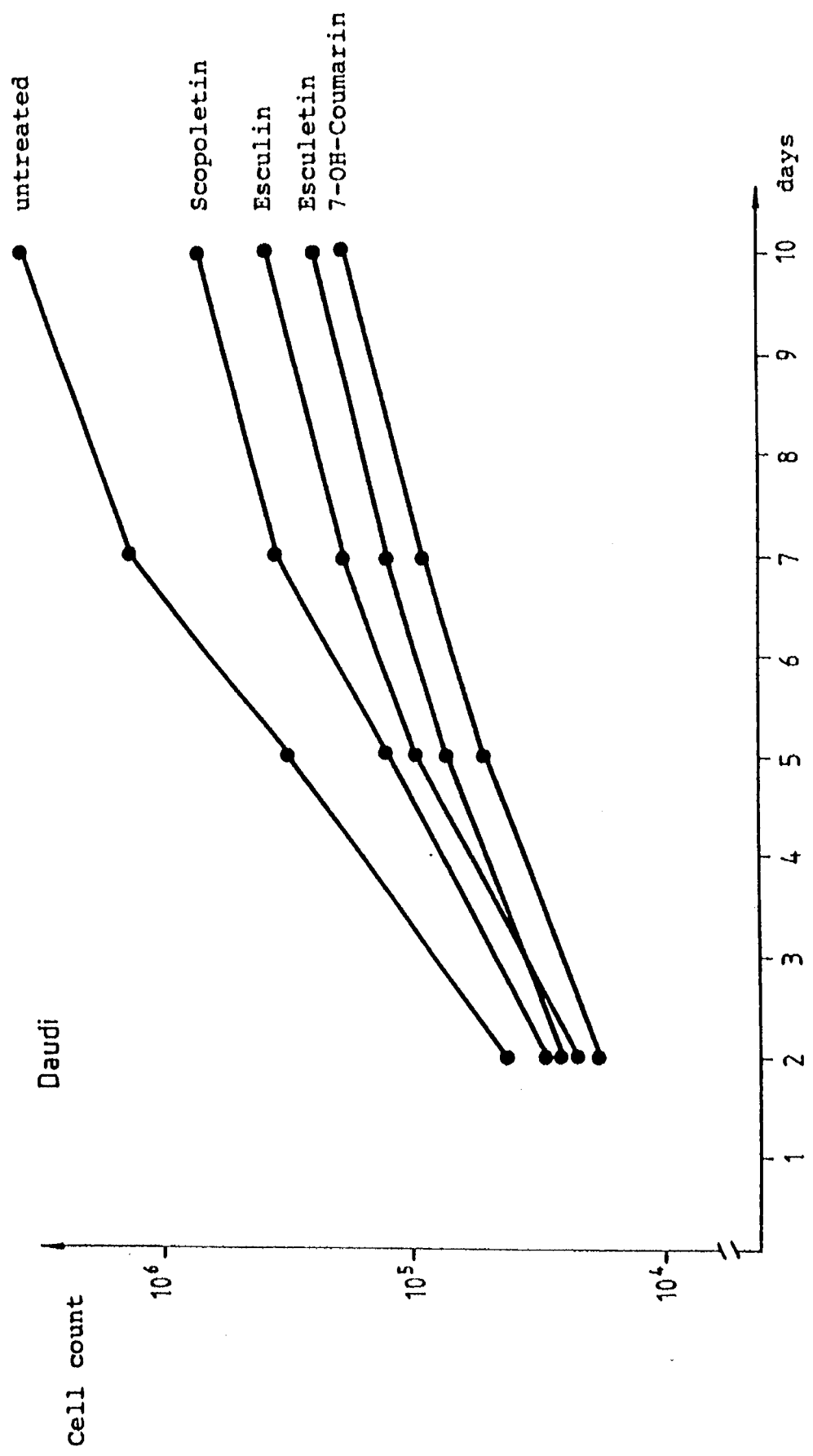
Fig. 14 Daudi

K 562

CAK I-1

HCV

GV-I

AtT 20

A-375

G-361

TREATING SUSCEPTIBLE HUMAN MALIGNANT TUMORS WITH 7-HYDROXY-1,2-BENZOPYRONE

This is a Rule 62 File Wrapper Continuation of application Ser. No.07/743,314, filed Aug. 16, 1991, now abandoned.

The invention relates to the use of 1,2-benzopyrone derivatives for producing medicaments for the therapeutic treatment of susceptible malignant tumors in humans.

The concepts currently available for oncological therapy include therapy with substances or radiation in order to thus achieve an immediate cell death and consequently a reduction in the volumes of primary tumor and/or metastases. With radiation-sensitive tumors this principle can be favourably implemented locally, whilst therapy with cytostatic/cytotoxic substances always acts systemically on the whole organism, if locoregional application is not technically possible. The concept of systemic cytostasis/cytotoxicity is limited in its biological efficiency by the range of current side-effects. Thus, attempts have been made, for example by modifying cytotoxic molecules such as cis-platinum to carbo-platinum, to reduce toxic side-effects to a tolerable level. A further modification principle is the addition of substances, such as hyaluronidase, verapramil and the like, which increase the biological effectiveness and others, with the aim of reducing the side-effects, to thus allow for a lower dosage of the cytostatic agent used. This concept has been successfully applied in individual protocols.

It has further been attempted to use substances which act through mechanisms other than direct cytostasis, or have available other mechanisms in addition to cytostasis. Thus it is known of cyclophosphamide that in low concentrations it inhibits the biological activity of T4 lymphocytes. Thus, an immunomodulation can be achieved with a cytostatic.

New therapy conceptions in oncology have concentrated in particular on natural substances which can be produced as pure substances either by plant extraction or by chemical synthesis. Thus it has been shown that coumarin inhibits malignant cell growth in cell cultures and in animal experiments, empirically verified side-effects in the case of mammals are to be disregarded compared with biological activity (cf. for example K. S. Zaenker, et al.: "Coumarin in melanoma patients, an experimental and clinical study", Drugs Exptl. Clin. Res. X (11) 767–774 (1984); M. E. Marshall et al., "Treatment of metastatic renal cell carcinoma with Coumarin (1,2-Benzopyrone) and Cimetidine, A pilot study", Journal of Clinical Oncology, 5, 862–866 (1987); D. Thornes et al., "Prevention of early recurrence of high risk malignant melanoma by coumarin" European Journal of Surgical Oncology 15, 431–435 (1989)).

It is the problem underlying the present invention to make available substances based on natural substances for the therapeutic treatment of or preventing the growth of a susceptible malignant tumors in humans, said substances being superior with regard to their biological activity to the already tested substances and simultaneously being toxicologically acceptable.

Figure 1:
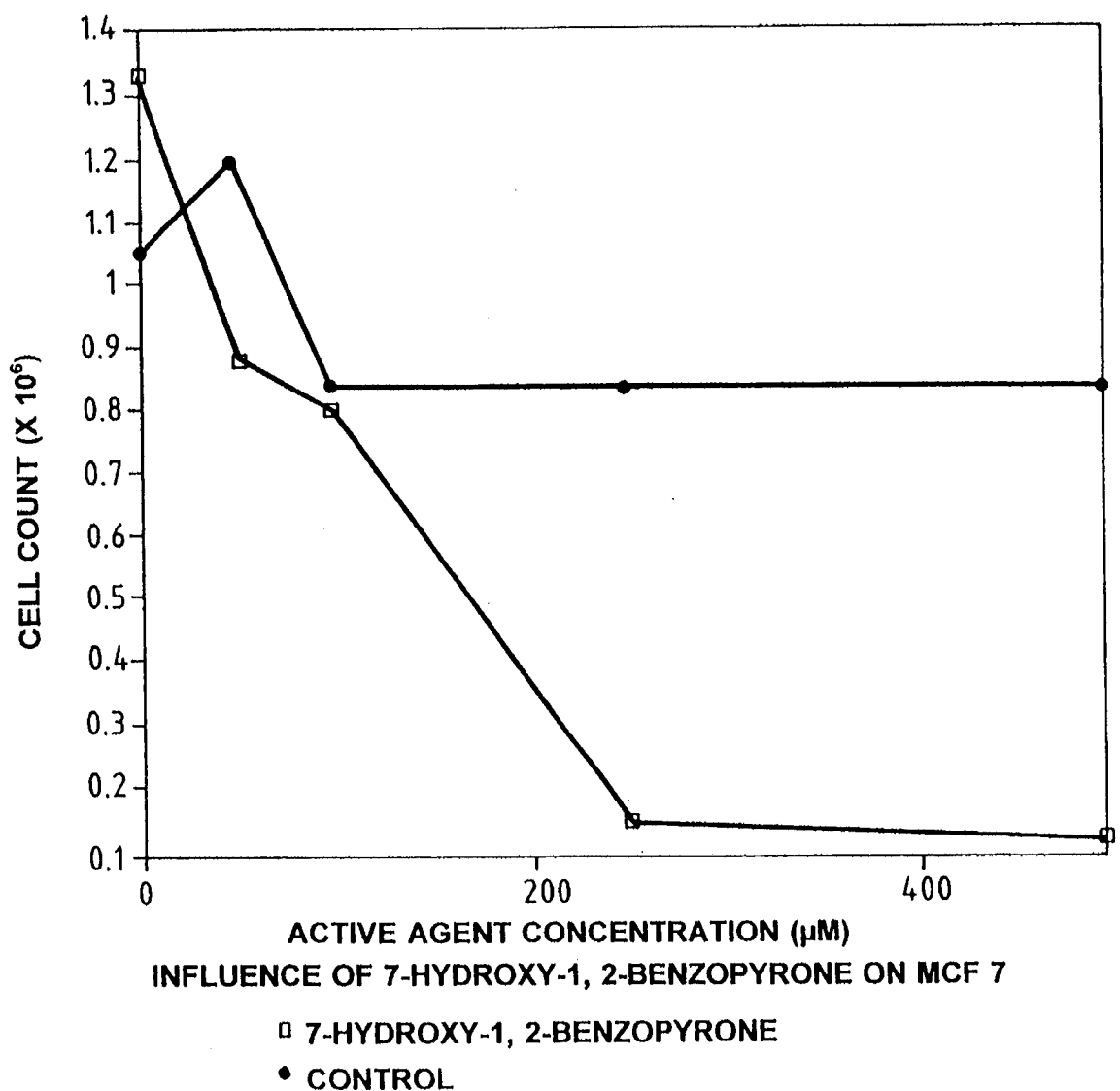
FIG. 1 is a graph showing the antiproliferative effect of various concentrations of 7-OH-1,2-BP in comparison with the control on MCF cells as in Example 2.

To solve the problem the use of 1,2-benzopyrone derivatives of the general formula

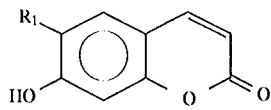

is proposed, in which $R_1$ is hydrogen, halogen or a hydroxy, sulphonyl, alkyl, hydroxyalkyl, acyloxy, alkoxy or benzyl group or a glycosidic group.

The alkyl groups in the optionally present alkyl, hydroxyalkyl, acyloxy or alkoxy groups are methyl, ethyl or propyl groups.

As glycosides, for example alpha and beta D-glucosides, especially beta D-glucopyranoside are considered.

Further, according to the invention, derivatives of 1,2-benzopyrone are especially suitable in which $R_1$ is an acyloxy group of the general formula

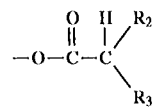

wherein $R_2$ is hydrogen, a hydroxy group or an amino group and $R_3$ hydrogen or a methyl, ethyl or propyl group.

According to the invention, especially preferred substances are those in which $R_1$ is hydrogen, a hydroxy group, a methoxy group or a beta D-glucopyranosyl group. Of these the first-named, i.e. 7-hydroxy-1,2-benzopyrone (7-OH-1,2-BP) is the most preferred.

The derivatives of 1,2-benzopyrone used according to the invention can be produced using known methods, c.f. Beilstein, E III/IV 18, 294 ff.

The compounds especially preferred according to the invention, namely 7-hydroxy-1,2-benzopyrone, 6,7-hydroxy-1,2-benzopyrone, 6-(beta-D-glucopyranosyloxy)-7-hydroxy-1,2-benzopyrone and 6-methoxy-7-hydroxy-1,2-benzopyrone are furthermore commercially available as natural substances.

Further, the synthetic production of the glycosides is possible, for example according to H. Wagner et al., Chem. Ber. 102, 3006 (1969).

Finally, the substances according to the invention can be produced enzymatically in a fermenter using processes well known to the expert.

It was surprisingly found that the derivatives of 1,2-benzopyrone according to the invention develop an unexpectedly high in-vivo activity with regard to the inhibition of the growth of tumor cells, the regress of tumors or the inhibition of metastases. As Tables 1 to 3 show, it was possible to demonstrate the growth-inhibiting activity of the derivatives according to the invention in-vivo on numerous tumor cells of varying origin.

TABLE 1

| Cell lines (human) Origin | Symbol | Conc. 7-OH-1,2-BP in growth medium μmol/ml | % Growth inhibition compared with control after x days |
|---|---|---|---|
| prostatic carcinoma | LNCap | 250 | 66 x = 10 |
| anaplastic astrocytoma | g-CCM | 200 | 44 x = 10 |
| anaplastic | g-UVW | 200 | 40 x = 10 |

TABLE 1-continued

| Cell lines (human) Origin | Symbol | Conc. 7-OH-1,2-BP in growth medium μmol/ml | % Growth inhibition compared with control after x days |
|---|---|---|---|
| astrocytoma | | | |
| breast carcinoma | MCF 7 | 200 | 64 x = 10 |
| bladder carcinoma | EJ | 200 | 26 x = 10 |
| Burkitt-lymphoma (leukemia) | Daudi | 1.2 | 94.8 x = 9 |
| glioblastoma | U 178 MG | 25 | 74 x = 12 |
| neuroblastoma | TP 410 N | 25 | 62 x = 12 |
| glioblastoma | TP 242 MG | 25 | 79 x = 12 |
| glioblastoma | TP 336 MG | 10 | 60 x = 12 |
| epidermoidal carcinoma | A 431 | 10 | 76 x = 12 |

It is of particular importance that the 1,2-benzopyrone derivatives used according to the invention, i.e. 7-hydroxy-1,2-benzopyrone and 6,7-hydroxy-1,2-benzopyrone and its 6-ether and -ester have a strong growth-inhibiting effect on brain-tumor cells (glioblastoma cells) (cf. tables 1 to 3 ), because previously neither chemotherapy, radiation treatment nor therapy with so-called BRM (Biological Response Modifiers) have had therapeutic success. Apart from the interferons, an in-vivo proliferation-inhibition of brain-tumor cells was shown for the first time with the substances according to the invention.

Figure 8:
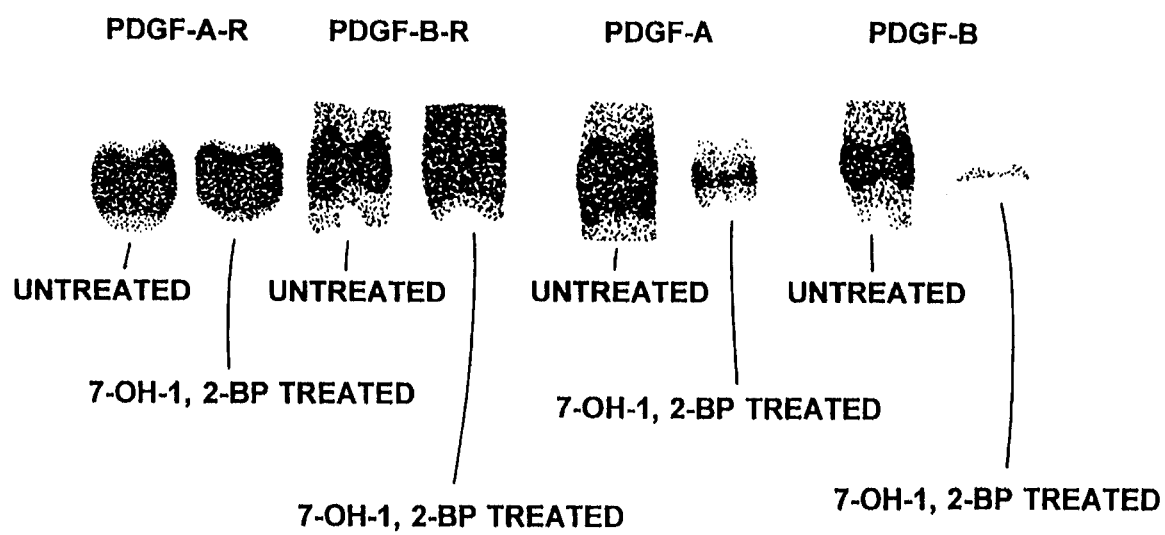

In connection with the neoplastic transformation and increased proliferation rate of glioblastoma cells, two autocrinic loops, the EGF and the PDGF system, are discussed. It was shown that, through 7-OH-1,2-BP, modifications occur at the level of gene expression of one of these systems. It was demonstrated (Seliger et al., unpublished results) that the transcription of the genes coding for PDFG-A and PDFG-B is inhibited (the corresponding mRNA-levels decrease, cf. FIG. 8), whilst the expression of the PDGF receptors and of the EGF system is not influenced. It is conceivable that the inhibition of the PDGF-mRNA induced by 7-OH- 1,2-BP is responsible for the observed growth-inhibition, an autocrinic loop being interrupted.

The 1,2-benzopyrone derivatives according to the invention are further particularly suitable for the treatment of renal, bladder, prostate, skin or lung carcinomas as well as leukemia.

The substances according to the invention can be used alone and also in combination with traditional therapeutics and with other methods for the treatment of malignant tumors.

Thus, a combination of the 1,2-benzopyrone derivatives according to the invention and chemotherapeutics such as cis-platinum and 5-fluorouracil (5-FU) showed unexpected synergistic effects (cf. Example 6).

The substances according to the invention can further be used in addition to traditional therapy with cytokines and monokins as well as in conjunction with radiation therapy, in order to increase the effectiveness thereof and to diminish the toxicity of the therapy scheme. It was shown on different cell lines from prostate carcinomas that using a combination of 7-OH-1,2-BP and tumor-necrosis-factor (TNF) leads to a super-additive inhibition of cell growth (cf. Example 7).

It was further found that in the case of hormone-dependent tumor cells, such as for example (LNCaP cells), the growth inhibition brought about by 7-OH-1,2-BP can be increased by additional hormone therapy in the traditional sense, for example with testosterone (cf. Example 8).

The use of the substances according to the invention can be considered for the prevention of malignant tumors and also for acute and adjuvant therapy.

In this connection it is also known that the survival time of patients whose tumors disproportionally express certain oncogenes such as "c-myc" and "H-ras", is lower than the survival time of tumor patients whose tumor does not display any increased oncogene expression. According to the invention it was now shown that the substances according to the invention and in particular 7-OH-1,2-BP inhibit the cell growth of tumor cells with oncogene-overexpression (cf. Example 12).

Figure 5:
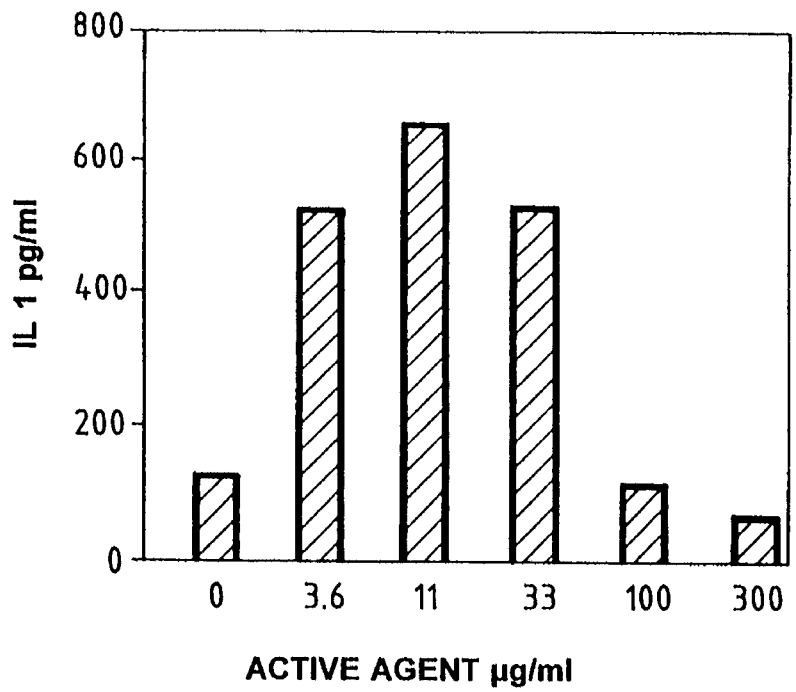
Figure 6:
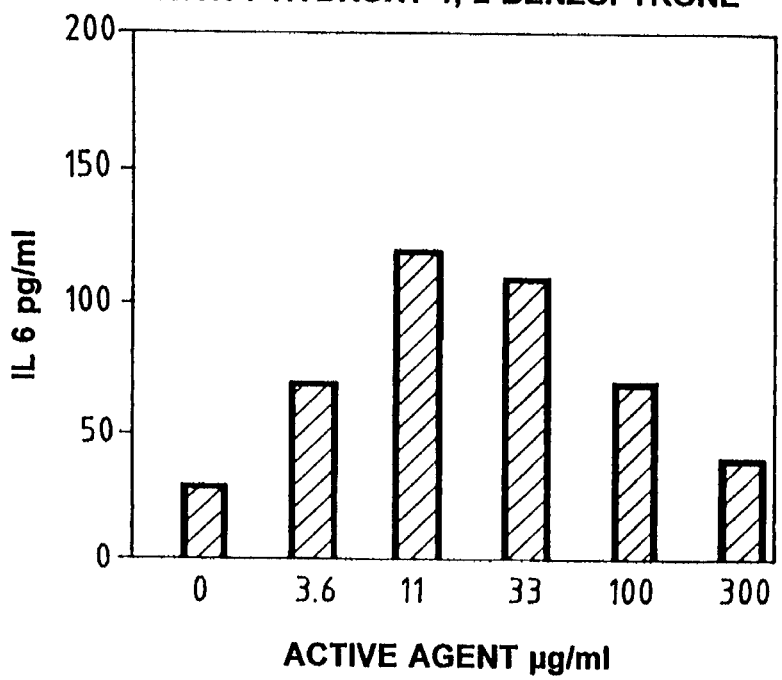
Figure 7A:
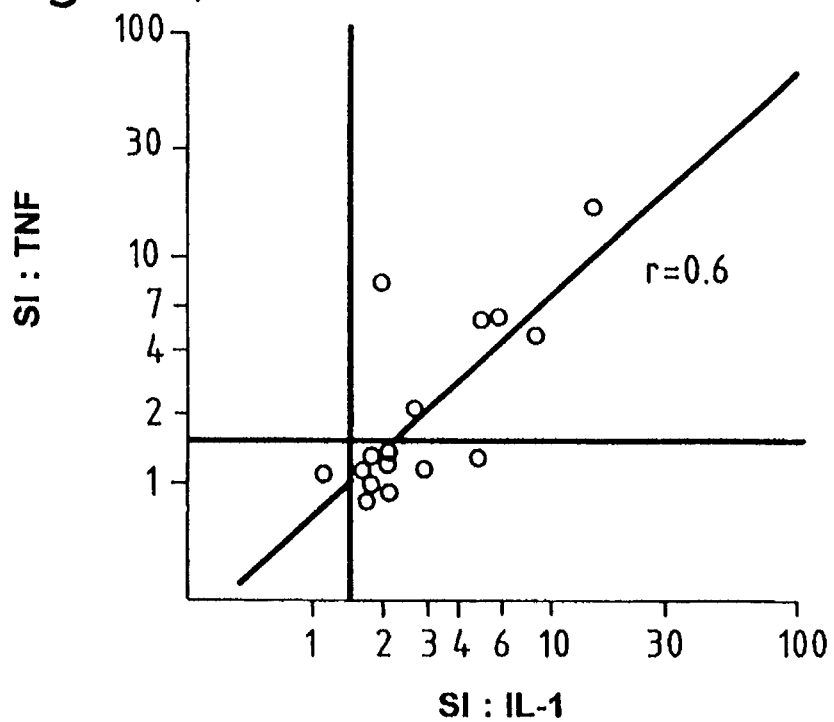
Figure 7B:
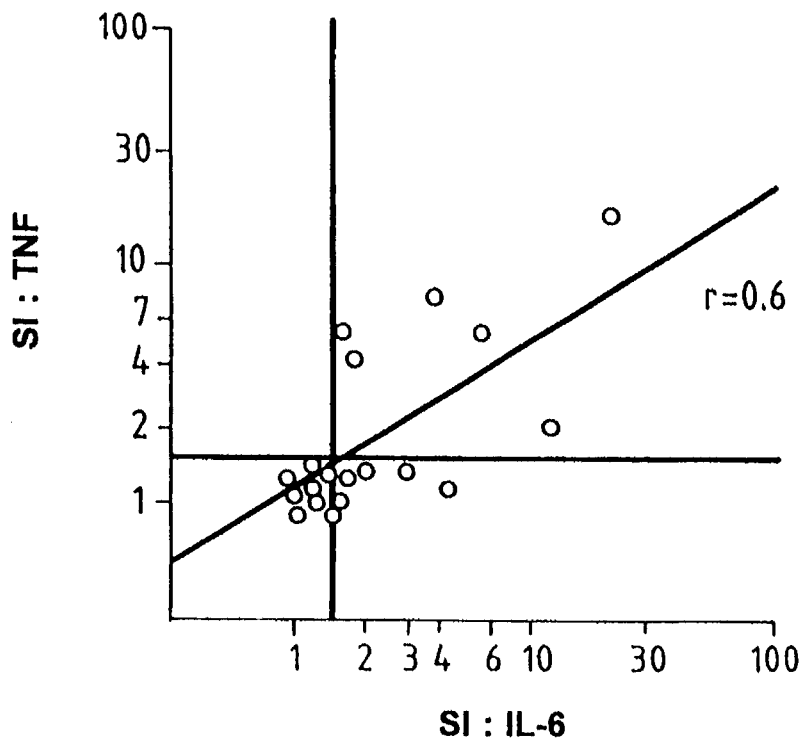

It was further discovered that low dosages of the 1,2-benzopyrone derivatives according to the invention have an immunomodulating effect (cf. Example 10 and FIGS. 5 to 7). In particular it was shown with human mononuclear cells (MNC) that the stimulation of the cells with combinations comprising 7-OH-BP and endotoxins such as lipopolysaccharides of bacterial origin results in a linked interaction of various cytokines. As FIG. 7 shows, a 10-fold increase in the Il-1 level leads to a 7-fold increase in the TNF-(tumor-necrosis-factor)level. Similar results were obtained for Il-6, although a 10-fold increase in the Il-6 level is accompanied by a 4-fold increase in the TNF-level.

In the case of the therapeutic treatment of malignant tumors, the point of emphasis is the growth-inhibiting properties of the substances according to the invention which come into effect at higher daily dosages of for example 300 to 6000 mg. This applies accordingly to treatment after primary therapy, to prevent a tumor relapse and metastasis formation.

Of particular importance—particularly regarding the hitherto usual therapies of malignant tumors—is the fact that no toxic side-effects of any kind were observed when the substances according to the invention were used on humans, even with long-term administration of extremely high dosages (7000 mg/daily, cf. Example 9).

The substances used according to the invention are accordingly, for the purposes of the invention, simultaneously highly effective and non-toxic.

As shown above, the 1,2-benzopyrone derivatives used according to the invention can be applied alone or in combination, preferably as fixed combination, with known cytostatics and/or cytokines. When they are administered alone, the daily dosage amounts vary, depending on the indication and therapeutic goal, between 50 and 300 mg if the immunomodulating effect is to be predominant and between300 and 6000 mg if emphasis is placed on the cytostatic aspect.

These dosage amounts can be administered in the form of the usual pharmaceutical preparations, such as for example solutions, dragees, capsules, tablets, injection or infusion solutions, orally or parenterally, such as for example intramuscularly, intra-arterially, intravenously and also topically such as for example in the form of transdermal plasters.

Sterile aqueous solutions which contain the active agent proposed according to the invention are suitable for application. These solutions can, if necessary, be buffered in a suitable manner; further, the liquid diluting agent can be isotonically set with sufficient salt solution or glucose.

To manufacture the medicaments on the basis of the 1,2-benzopyrone derivatives used according to the invention, the usual carriers and additives can be used. Usual carriers are e.g. water, physiological cooking salt solution, alcohols, polyethylene glycols, glycerin ester, gelatine, carbohydrates such as lactose and starch, calcium carbonate, magnesium stearate, talcum. Usual additives are e.g. preservatives, lubricants, wetting agents and emulsifiers, colorants, flavourings and aromatic substances. The choice of the carriers and additives depends on whether the preparations according to the invention are to be applied enterally, parenterally or locally.

The invention will be illustrated in the following with reference to Examples:

EXAMPLE 1

Growth-inhibiting effect of 7-hydroxy-1,2-benzopyrone on various tumor cell lines—comparison with coumarin The following cell lines were investigated:

| | |
|---|---|
| Glioblastoma | U 178 MG |
| Neuroblastoma | TP 410 N |
| Glioblastoma | TP 242 MG |
| Glioblastoma | TP 336 MG |
| Epidermoidal carcinoma | A 431 |

The neuroblastoma cell line and the three glioblastoma cell lines were cultivated in Ham's F10 medium enriched with 10% fetal calf serum (FCS) and the usual quantity of penicillin, streptomycin (Pen/Strep) and glutamine. The epidermoidal cell line was cultivated in modified Eagle's Medium (MEM), likewise enriched with 10% (FCS) and the usual quantity of glutamine and Pen/Strep.

In a pre-trial, $5\times10^3$ cells of each line were in each case initially plated out in 96-well-plates and incubated for 48 hours with differing concentrations, namely 150 μmol 75 μmol 1, 37.5 μmol, 18 μmol and 9 μmol for each ml 7-hydroxy-1,2-benzopyrone medium. Untreated cells served as a control. Subsequently, the cells were incubated for 8 hours with $^3$H-thymidine. The radioactivity absorbed by the cells was measured in the usual way. It was shown that the TP 336 and A 431 lines were more sensitive to (7-OH-1,2-BP) than were U 178, TP 242 and TP 410 N. The 37.5 μM/ml concentration of the active substance was, however, not cytotoxic for any of the cells, but cytostatic.

On the basis of these results a growth curve over a period of 12 days in all was established for the said cell lines, the lines TP 336 MG and A 431 being incubated under the above-described conditions with 10 μM/ml 7-OH-1,2-BP in each case, whilst 25 μM/ml of the active substance was used with the lines TP 242 MG, TP 410 N and U 178 MG. In each case $5\times10^4$ cells were plated out in $T_{25}$ bottles, the untreated cells being incubated in analogous conditions as control. The cell count was microscopically determined after 3, 5, 7, 10 and 12 days.

The results are given below in Table 2.

TABLE 2

| Cell line | Conc. (μM/ml) 7-OH- 1,2-BP | Cell count (× 10$^4$) after | | | | | % growth inhibition compared with control after 12 days |
|---|---|---|---|---|---|---|---|
| | | 3 | 5 | 7 | 10 | 12 days | |
| U 178 MG | 25 | | 15 | 13 | 26 | 2737 | 74% |
| Control | | 23 | 57 | 84 | 91 | 141 | |
| TP 410 N | 25 | | 8 | 20 | 36 | 4250 | 62% |
| Control | | 25 | 45 | 71 | 97 | 132 | |
| TP 242 MG | 25 | 4 | 6 | 8 | 10 | 12 | 79% |
| Control | | 10 | 15 | 23 | 49 | 57 | |
| TP 336 MG | 10 | 7 | 11 | 22 | 18 | 18 | 60% |
| Control | | 13 | 25 | 39 | 34 | 45 | |
| A 431 | 10 | 4 | 10 | 3 | 12 | 21 | 76% |
| Control | | 6 | 24 | 45 | 56 | 87 | |

The table shows that a clear inhibition occurred for all cell lines studied; in the case of TP 242 MG with 25 μM/ml, a nearly 80% inhibition of proliferation was observed compared with the control. Of particular importance is the growth-inhibition of the brain-tumor cells U 178 MG, TO 410 N, TP 242 MG and TP 336 MG, which—except for interferons—previously could not be achieved with any available substance.

Comparative trial

The production of the growth curve was repeated with the exception that, instead of 7-OH-1,2-BP, coumarin was used in the corresponding concentrations.

Not only in the pre-trial, but also in the formulations for the production of a growth curve, no significant difference could be observed between the cell samples treated with coumarin and the control.

Only 7-hydroxy-1,2-benzopyrone, but not the compound unsubstituted in 7-position, developed growth-inhibiting activity on the investigated cell lines.

EXAMPLE 2

Growth-inhibiting effect of 7-OH-1,2-BP on breast cancer cells

The MCF 7 cell line from breast cancer was cultivated in DMEM-S 10, enriched with 10% FCS, for 10 days in the usual way. The cells were subsequently incubated with the concentrations of 7-OH-1,2-BP given in FIG. 1 and subsequently the survival rate and the cell count were photometrically determined with the ethidium-bromide/acridine orange process in the known manner. The results are given in FIG. 1.

They clearly show the cytostatic effect of 7-OH-1,2-BP on breast cancer cells.

EXAMPLE 3

Antineoplastic effect of 7-OH-1,2-BP on human anaplastic astrocytoma cells

Figure 2:
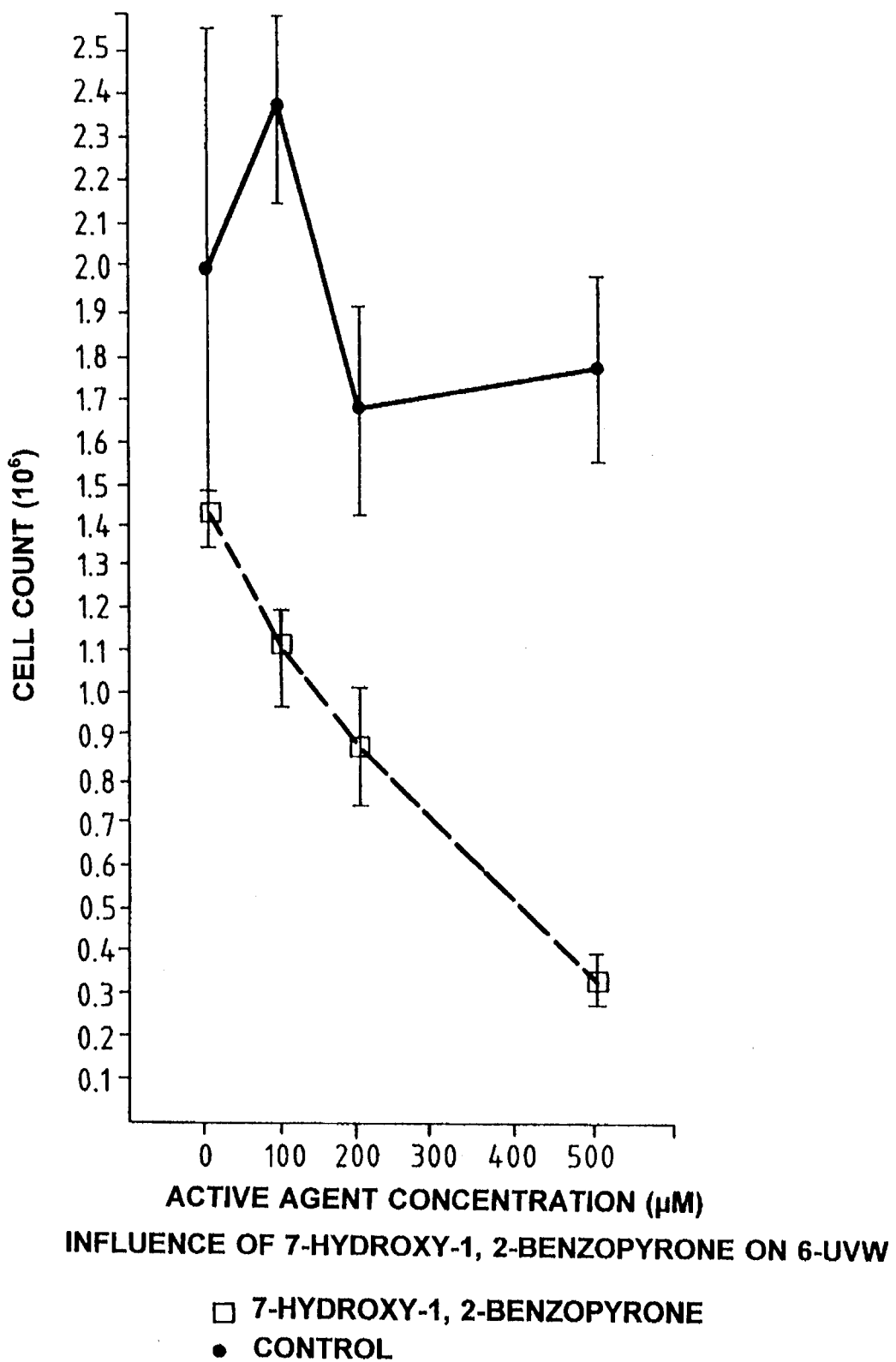

The process as per Example 2 was repeated with the exception that cells of the 6-UVW line from human anaplastic astrocytoma were used and enriched in DMEM-:HAM's F 12 medium (1:1) with L-glutamine and 10% FCS. The results are given in FIG. 2.

They show that 7-OH-1,2-BP also has a cytostatic effect on human anaplastic astrocytoma cells.

EXAMPLE 4

Growth-inhibiting effect of 7-hydroxy-1,2-benzopyrone and derivatives of the same on various tumor cell lines The effect of 7-hydroxy-1,2-benzopyrone (7-OH-coumarin), 6,7-hydroxy-1,2-benzopyrone(esculetin),6-beta-D-glucopyranosyloxy- 7-hydroxy-1,2-benzopyrone (esculin) and 6-methoxy-7-hydroxy-1,2-benzopyrone (scopoletin) were investigated on the following cell lines:

| | |
|---|---|
| Glioblastoma | Tp 242 MG |
| | Tp 483 MG |
| Neuroblastoma | Tp 410 N |
| Leukemic | K 562 |
| | Daudi |
| Hypernephroma | CAK I-1 |
| | CAK I-2 |
| Bladder tumor | HCV |
| Breast cancer | MCF-7 |
| | Z-R-75-1 |

-continued

| | |
|---|---|
| Prostate carcinoma | GV 1 |
| | At T-20 |
| Melanoma | A-375 |
| | G-361 |

The cell lines were cultivated as indicated in Example 1.

The antiproliferative effect of the 1,2-benzopyrone derivatives according to the invention on the tumor cell lines in each case was shown with the help of the $^3$H-thymidine insertion and with reference to growth curves.

$^3$H-thymidine assay

In a 24-well-plate, in each case $10^4$ cells of the line to be investigated were inoculated per well. Approximately 48 hours later the cells were half-confluent; the medium was then changed and replaced by a medium containing the active substance in question (cf Table 3). After a further 48 hours 0.25 µCi $^3$H-thymidine (Ammersham) was added to each well and the cells were incubated for a further 24 hours. Subsequently the cultures were washed twice with ice-cold PBS and the high-molecular-weight $^3$H-radioactivity was precipitated with 5% trichloroacetic acid for one hour at 4° C. After the washing of the cells in PBS the $^3$H-radioactivity was solubilized with 0.3M NaOH and measured in the counter. The growth-inhibition was determined by comparing the thymidine insertion of the cells treated with active substance with untreated cells. The results are given in table 3 below.

TABLE 3

| Active substance concentration | $^3$H-thymidine insertion (%) of control | | | |
|---|---|---|---|---|
| (µM/ml) | 7-OH-1,2-BP | Esculetin | Esculin | Scopoletin |
| A) Glioblastoma cells Tp 242 MG/Tp 483 MG | | | | |
| 1 | 93/97 | 96/98 | 100/99 | 99/100 |
| 2 | 91/95 | 96/94 | 98/97 | 93/95 |
| 4 | 91/89 | 89/85 | 95/89 | 85/89 |
| 8 | 84/81 | 87/77 | 81/83 | 87/86 |
| 16 | 73/69 | 75/73 | 73/74 | 84/78 |
| 25 | 55/66 | 72/69 | 68/66 | 79/72 |
| 50 | 43/39 | 60/62 | 65/54 | 74/67 |
| 100 | 39/32 | 44/55 | 61/51 | 61/63 |
| 250 | 35/27 | 32/39 | 53/48 | 52/54 |
| 500 | 32/25 | 21/28 | 49/45 | 48/50 |
| B) Neuroblastoma cells TP 410 N | | | | |
| 1 | 96 | 94 | 100 | 100 |
| 2 | 91 | 86 | 96 | 98 |
| 4 | 80 | 75 | 85 | 95 |
| 8 | 73 | 69 | 76 | 87 |
| 16 | 67 | 64 | 69 | 82 |
| 25 | 50 | 48 | 62 | 74 |
| 50 | 48 | 42 | 54 | 71 |
| 100 | 42 | 40 | 43 | 65 |
| 250 | 36 | 34 | 38 | 62 |
| 500 | 21 | 29 | 30 | 54 |

| Active substance concentration | $^3$H-thymidine tracer (%) of control | | | |
|---|---|---|---|---|
| (µM/ml) | 7-OH-1,2-BP | Esculetin | Esculin | Scopoletin |
| C) Leukemic cells Daudi/K-562 | | | | |
| 1 | 98/100 | 94/97 | 100/100 | 96/100 |
| 2 | 89/91 | 96/95 | 98/100 | 94/97 |
| 4 | 82/84 | 83/84 | 93/96 | 80/90 |
| 8 | 76/76 | 75/77 | 87/88 | 79/85 |
| 16 | 63/67 | 69/62 | 80/81 | 71/82 |
| 25 | 54/53 | 63/58 | 71/72 | 64/71 |
| 50 | 49/47 | 61/50 | 69/70 | 58/66 |
| 100 | 38/42 | 57/47 | 52/58 | 53/52 |
| 250 | 35/39 | 54/44 | 48/51 | 49/47 |
| 500 | 28/37 | 39/31 | 44/40 | 41/44 |
| D) CAKI cells CAKI-1/CAKI-2 | | | | |
| 1 | 100/95 | 96/98 | 100/99 | 100/99 |
| 2 | 98/92 | 93/94 | 94/96 | 98/96 |
| 4 | 90/88 | 88/90 | 92/90 | 87/84 |
| 8 | 81/77 | 80/87 | 83/84 | 81/80 |
| 16 | 76/71 | 62/82 | 78/73 | 80/76 |
| 25 | 62/65 | 58/69 | 74/72 | 73/71 |
| 50 | 57/54 | 53/65 | 65/66 | 69/66 |
| 100 | 49/46 | 45/54 | 60/50 | 67/61 |
| 150 | 44/39 | 40/53 | 53/56 | 62/59 |
| 500 | 40/35 | 32/50 | 47/52 | 55/53 |
| E) HCV cells | | | | |
| 1 | 98 | 99 | 100 | 97 |
| 2 | 95 | 94 | 98 | 90 |
| 4 | 88 | 87 | 95 | 86 |
| 8 | 82 | 83 | 89 | 81 |
| 16 | 74 | 78 | 86 | 77 |
| 25 | 69 | 76 | 83 | 69 |
| 50 | 63 | 71 | 79 | 65 |
| 250 | 57 | 64 | 76 | 60 |
| 500 | 50 | 62 | 75 | 57 |
| F) Breast cancer cells MC 7/Z-R-75-1 | | | | |
| 1 | 98/96 | 100/98 | 99/100 | 100/98 |
| 2 | 94/91 | 98/96 | 91/97 | 97/96 |
| 4 | 88/82 | 92/89 | 88/89 | 94/91 |
| 8 | 82/73 | 85/84 | 80/85 | 86/83 |
| 16 | 75/65 | 76/77 | 71/75 | 81/79 |
| 25 | 69/55 | 69/70 | 69/72 | 76/72 |
| 50 | 62/49 | 64/61 | 62/64 | 73/64 |
| 100 | 51/43 | 58/53 | 51/56 | 69/57 |
| 250 | 43/39 | 50/46 | 49/51 | 62/55 |
| 500 | 29/27 | 42/39 | 42/47 | 54/50 |
| G) Prostate carcinoma cells GV-1/At T 20 | | | | |
| 1 | 100/98 | 97/93 | 97/100 | 100/98 |
| 2 | 89/89 | 93/89 | 95/94 | 98/94 |
| 4 | 83/85 | 88/86 | 85/89 | 91/89 |
| 8 | 75/78 | 84/75 | 84/83 | 88/84 |
| 16 | 69/65 | 78/75 | 79/72 | 82/76 |
| 25 | 63/60 | 75/67 | 76/69 | 78/68 |
| 50 | 51/62 | 63/62 | 68/64 | 71/62 |
| 100 | 39/44 | 60/55 | 60/58 | 63/57 |
| 250 | 36/38 | 58/49 | 51/49 | 61/49 |
| 500 | 27/31 | 50/44 | 43/44 | 51/43 |
| H) Melanoma cells A-375/G-361 | | | | |
| 1 | 100/94 | 98/97 | 100/98 | 99/100 |
| 2 | 92/91 | 91/93 | 96/94 | 96/98 |
| 4 | 86/77 | 89/90 | 93/90 | 90/96 |
| 8 | 81/77 | 84/88 | 87/86 | 89/88 |
| 16 | 72/74 | 75/72 | 82/81 | " |
| 25 | 64/68 | 70/68 | 78/74 | 87/85 |
| 50 | 53/58 | 65/60 | 71/70 | 78/85 |
| 100 | 49/53 | 63/58 | 64/63 | 75/76 |
| 250 | 47/42 | 59/52 | 60/60 | 75/71 |
| 500 | 44/38 | 55/49 | 57/54 | 70/67 |

Producing growth curves

The growth curves of the cell lines in each case were determined in the presence of the active substances given below and compared with controls which had been cultivated without active substance, The active substance concentration in each case was so chosen that $^3$H-thymidine insertion was 50% inhibited. The active substance concentrations used under this aspect for the active substances and cell lines in each case are given in table 4 below in µM/ml,

TABLE 4

| Cell lines | 7-OH-C | Esculetin | Esculin | Scopoletin |
|---|---|---|---|---|
| Tp 242 MG | 25 | 75 | 500 | 500 |
| Tp 483 MG | 25 | 150 | 100 | 500 |
| Tp 410 N | 25 | 25 | 75 | 500 |
| K 562 | 50 | 50 | 250 | 175 |
| Daudi | 50 | 250 | 100 | 250 |
| CAKI-1 | 100 | 50 | 375 | 500* |
| CAKI-2 | 75 | 500 | 500* | 500* |
| HCV | 500 | 500* | 500* | 500* |
| MCF-7 | 100 | 250 | 100* | 500* |
| Z-R-75-1 | 50 | 175 | 250 | 500* |
| GV-I | 75 | 500 | 250 | 500 |
| At T 20 | 50 | 250 | 250 | 250 |
| A-375 | 100 | 500* | 500* | 500* |
| G-361 | 125 | 500 | 500* | 500* |

*Maximum active-substance dosage which can be used but does not lead to a 50% growth inhibition.

To produce the growth-curves, in each case $10^4$ cells were inoculated per plate and incubated in the presence of the active substance in question or as a control. After 2, 5, 7 and 10 days the cell count was microscopically determined. The results are given in FIGS. 12 to 24.

The values given there represent the average cell count of three parallel formulations in each case.

EXAMPLE 5

Inhibition of the growth of bladder tumor and erythroleukemic cells by 7-OH-1,2-BP Cells from 3 different bladder tumors as well as erythroleukemic cells (K 562) were incubated in 3 parallel test-formulations for 20 hours with increasing concentrations of 7-OH-1,2-BP (cf. FIG. 3) in each case in 96-well-plates, washed and mixed with medium. Subsequently the cell count was photometrically determined according to Alley M. C. et al., Cancer Research 48, 589–601 (1988). In the process, a colorant is added to the cells that have been mixed with medium, the colorant being so converted by cells with mitochondrial activity that a photometric determination of the cell count is possible.

Figure 3:
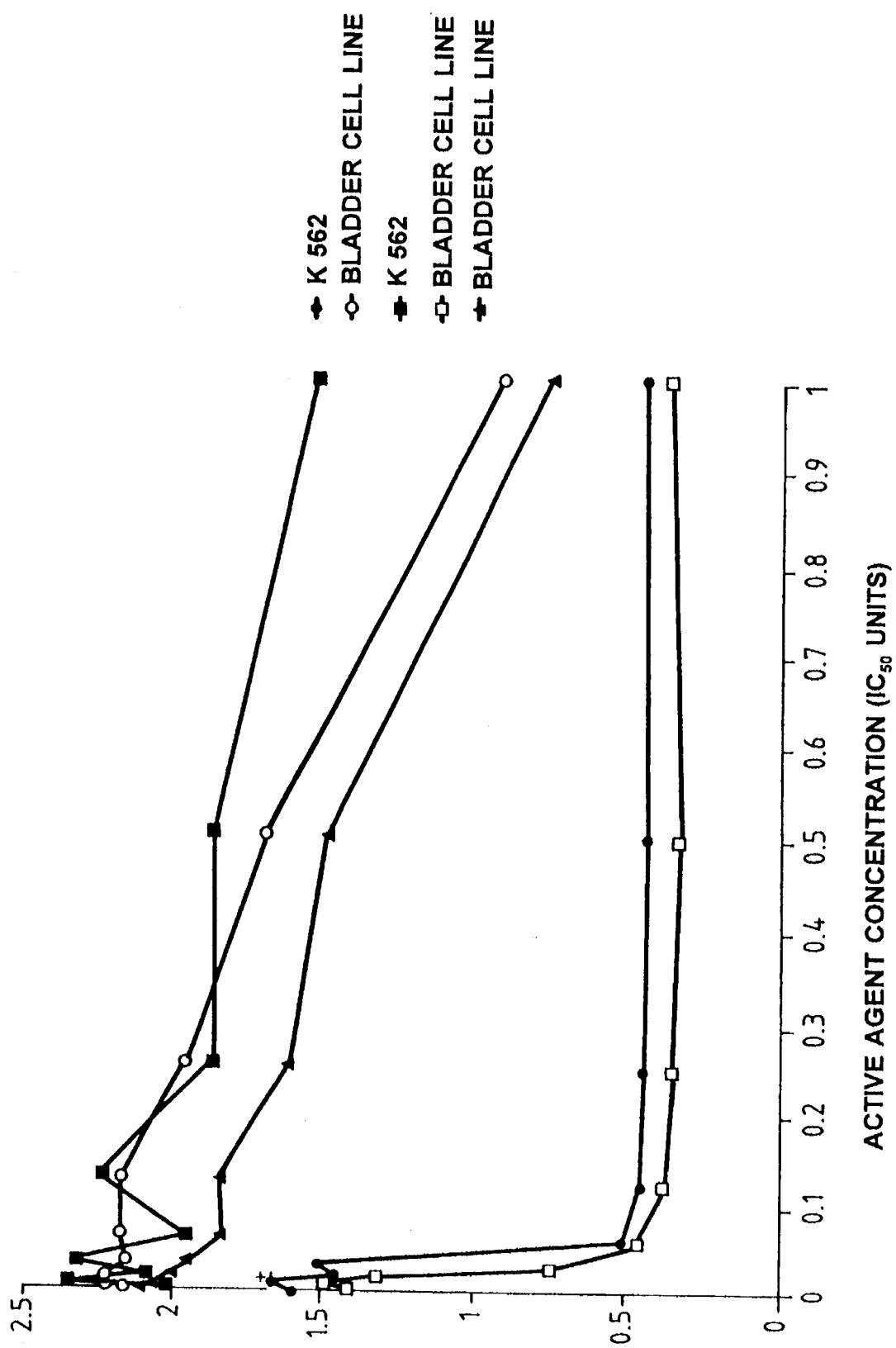

The results are given in FIG. 3.

They show that, in the case of the cell lines investigated, a dosage-related inhibition of the mitochondrial activity occurs, which can be causally attributed to cell-growth inhibition.

EXAMPLE 6

Synergistic effect of 7-OH-1,2-BP in combination with 5-fluorouracil (5-FU) and with cis-platinum Cells from a colon adenocarcinoma and from a bronchoalveolar carcinoma were used. The cells were cultivated, and the synergistic effectiveness during the cell-growth inhibition of 7-OH-1,2-BP, in each case in combination with 5-FU and with cis-platinum, was examined according to the method described by Steel, Int. J. Radiat. Oncol. Biol./Phys. 5, 85–91 (1979).

For this purpose, firstly individual dosage-response curves were plotted in each case for 5-FU, cis-platinum and 7-OH-1,2-BP with reference to cell-growth inhibition. Subsequently, for each of the combinations, the points of equal biological activity were taken from both of the curves and were used as reference points for those dosage amounts which were to be used in a combination test (5-FU+7-OH-1,2-BP or cis-platinum+7-OH-1,2-BP). With these concentrations dosage response curves were once again plotted.

Figure 4:
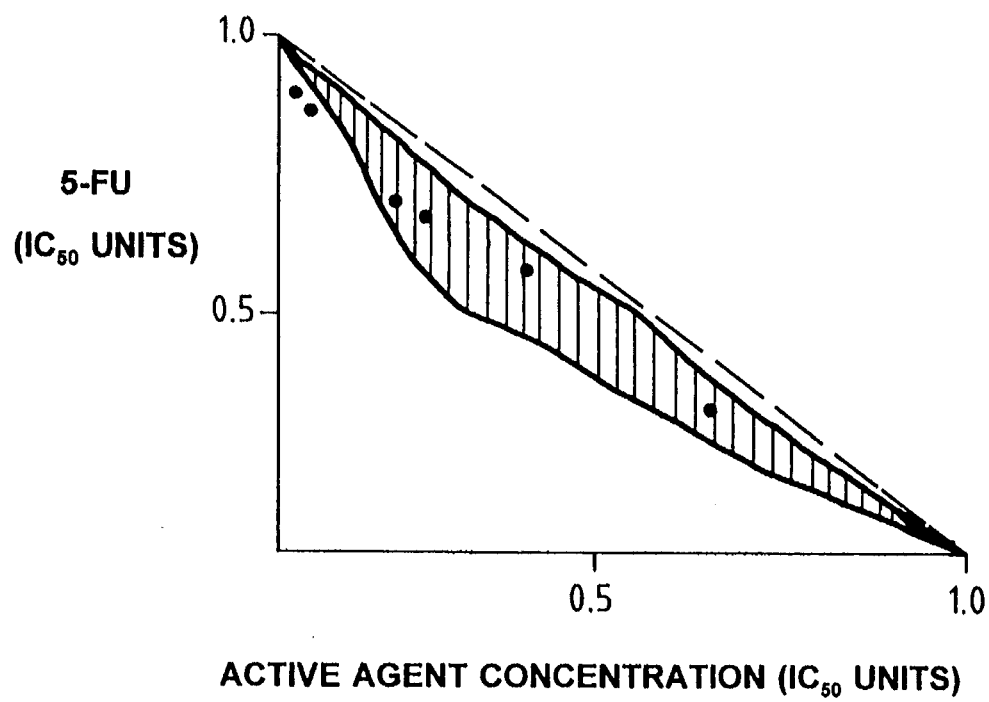
Figure 4:
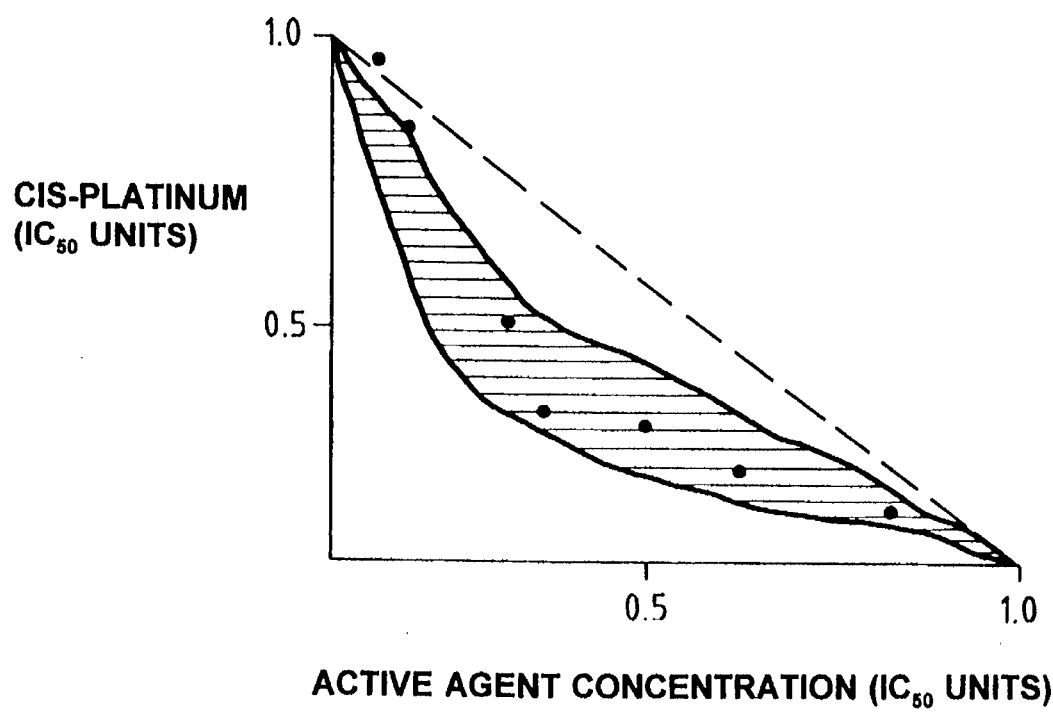

The results are given in FIG. 4a) and 4b).

They show that both combinations develop a synergistic effect during the inhibition of the cell growth of the cell lines investigated.

EXAMPLE 7

Synergistic effect of 7-OH-1,2-BP in combination with tumor-necrosis-factor (TNF)

Various cell lines (DU-145, PC-3 and LNCaP) from prostate carcinomas were used.

Cell growth was determined as in Example 1 in a well plate, the cells being cultivated with 7-OH-1,2-BP alone, TNF alone, the combination of 7-OH-1,2-BP and TNF and also without the addition of active substance (control).

The results are given in table 5 below.

TABLE 5

| Cell line | Control | 7-OH-1,2-BP (500 µM/ml) | TNF (1 nM/ml) | 7-OH-1,2-BP (500 µM/1 nM) |
|---|---|---|---|---|
| DU-145 | 51.86 + 3.06 | 38.30 + 2.92 | 55.39 + 0.68 | 29.97 + 3.69 |
| PC-3 | 18.58 + 1.05 | 11.51 + 0.63 | 18.39 + 0.74 | 6.97 + 0.13 |
| LNCaP | 61.40 + 3.70 | 11.0 + 1.10 | 15.60 + 2.50 | 1.60 + 0.99 |

Initial cell count: $3 \times 10^4$ cells/well; exposure period: DU-145, PC-3: 4 days; LNCaP: 6 days The results show that the combination of 7-OH-1,2-BP with TNF leads to a super-additive inhibition effect on cell growth.

EXAMPLE 8

Increasing growth inhibition by combining 7-OH-1,2-BP and testosterone

LNCaP cells were cultivated as described in the previous Examples in a well plate, with the exception that the medium had been previously freed, using charcoal, of any androgynous substances possibly present.

Figure 9:
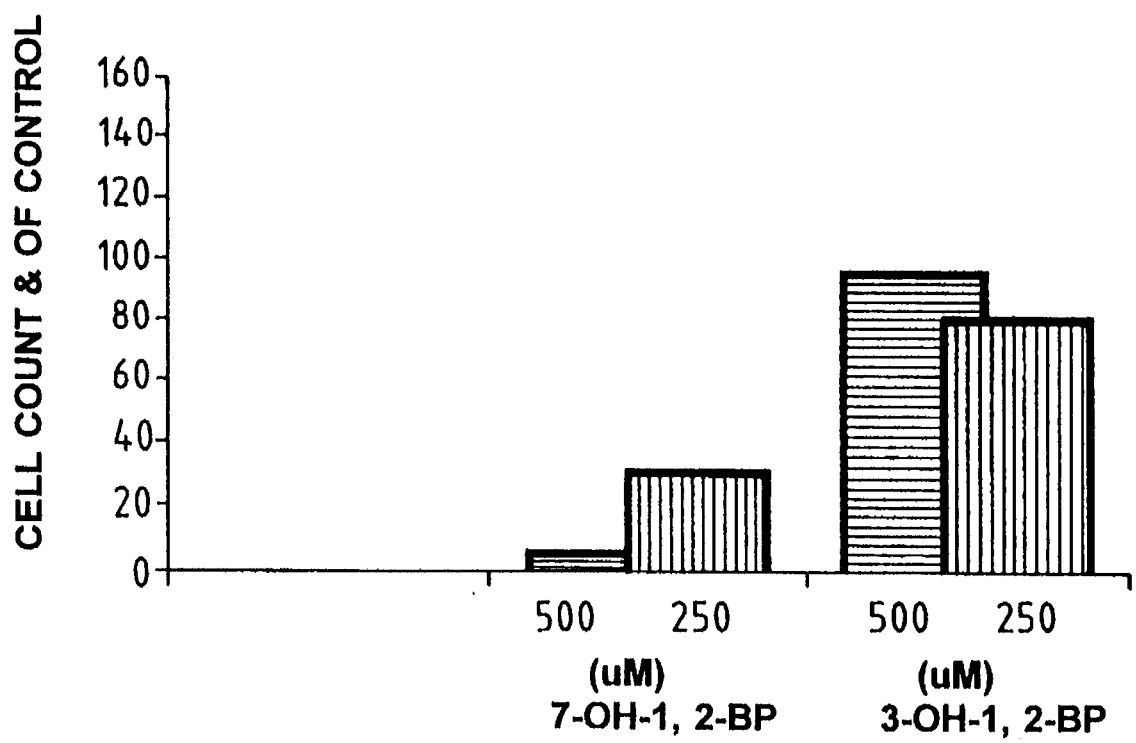
Figure 15:
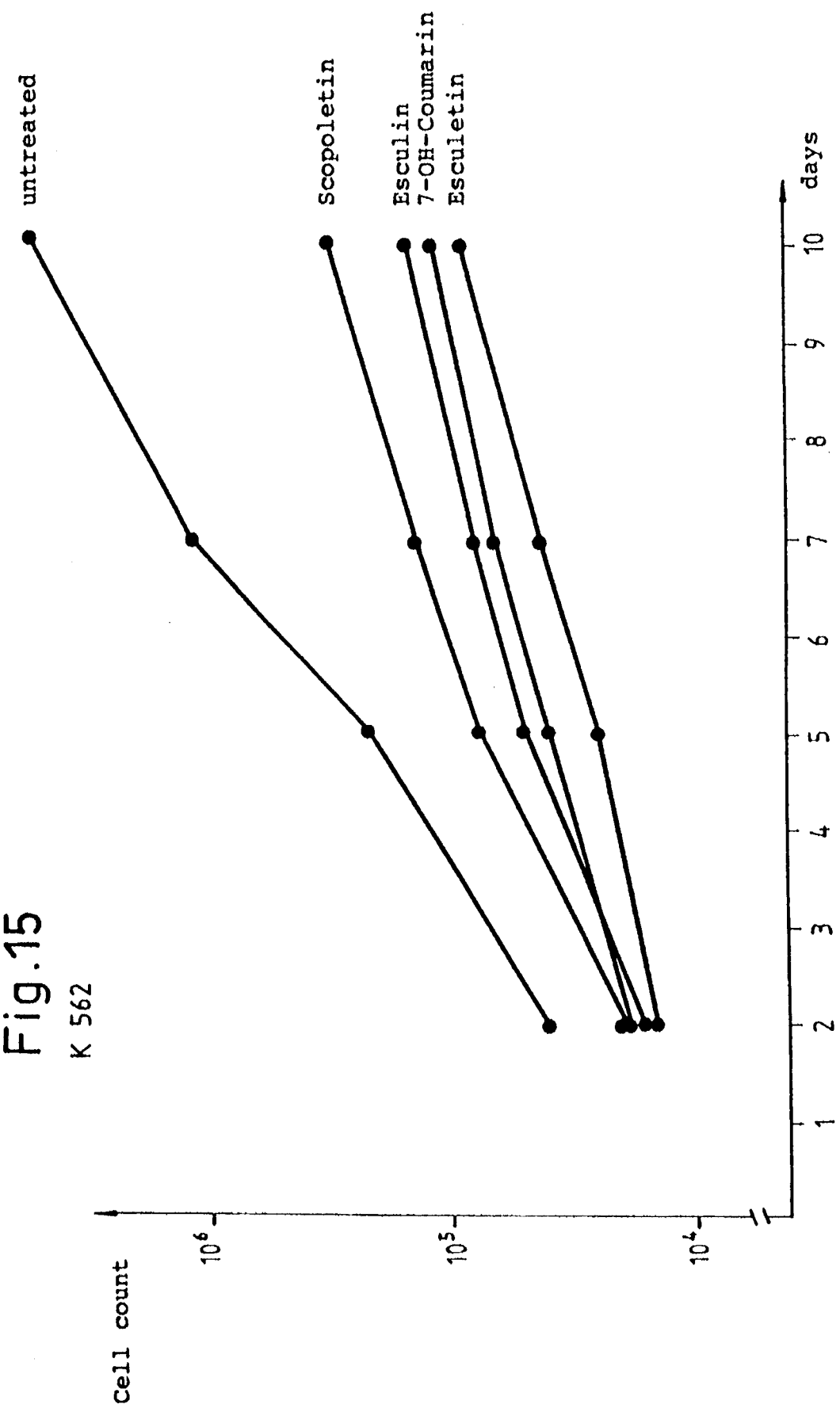
Figure 16:
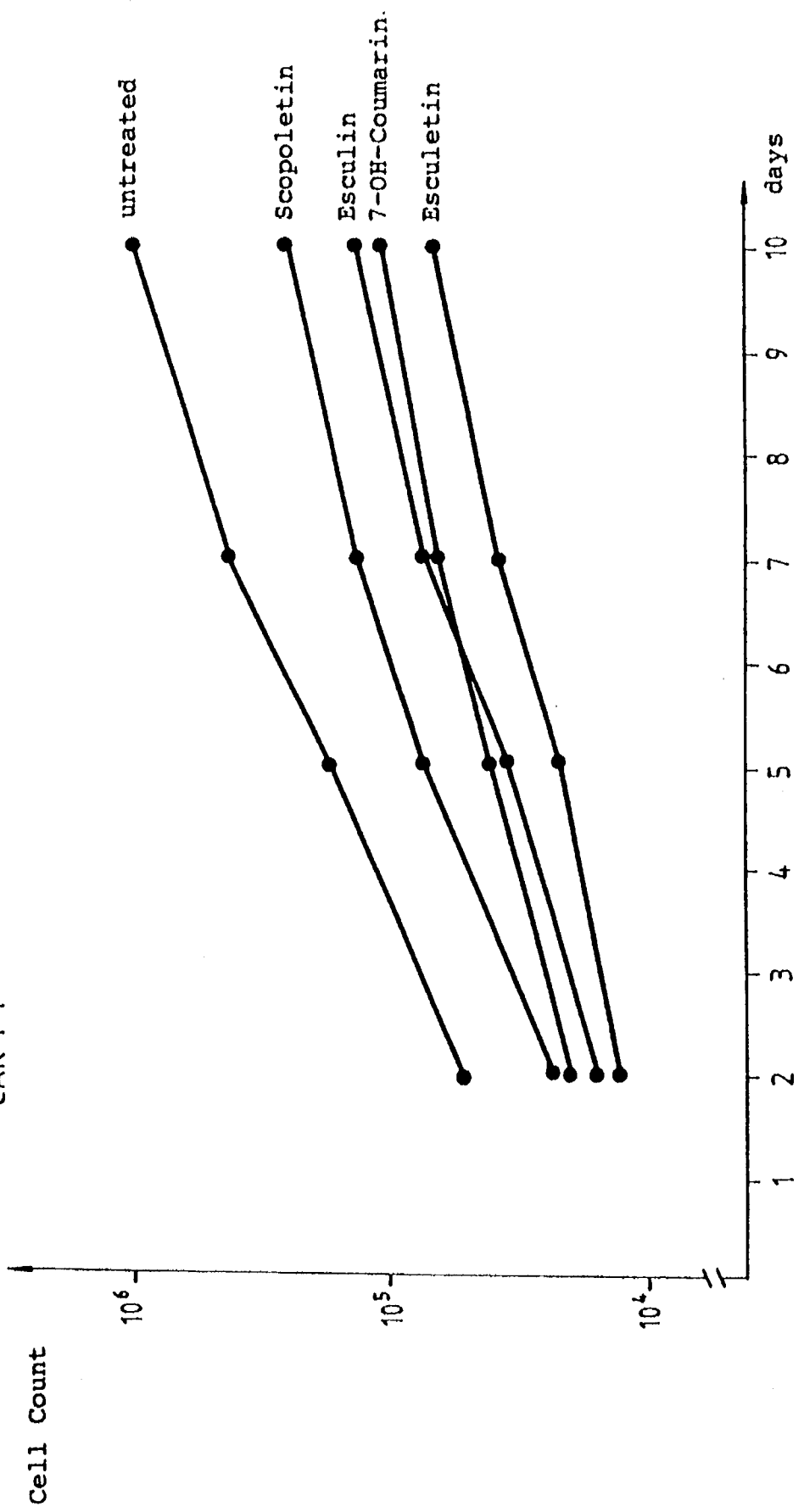
Figure 17:
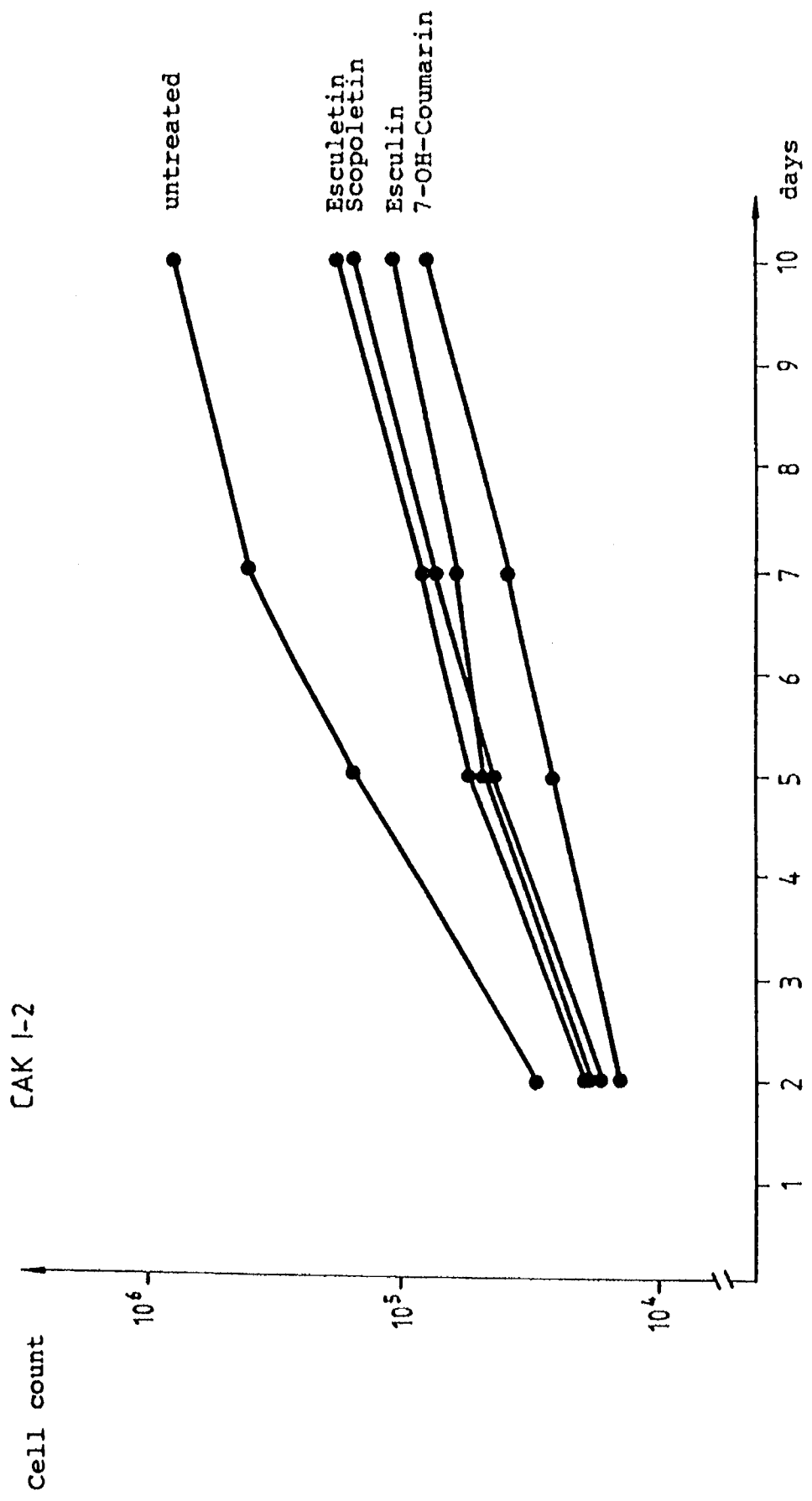
Figure 18:
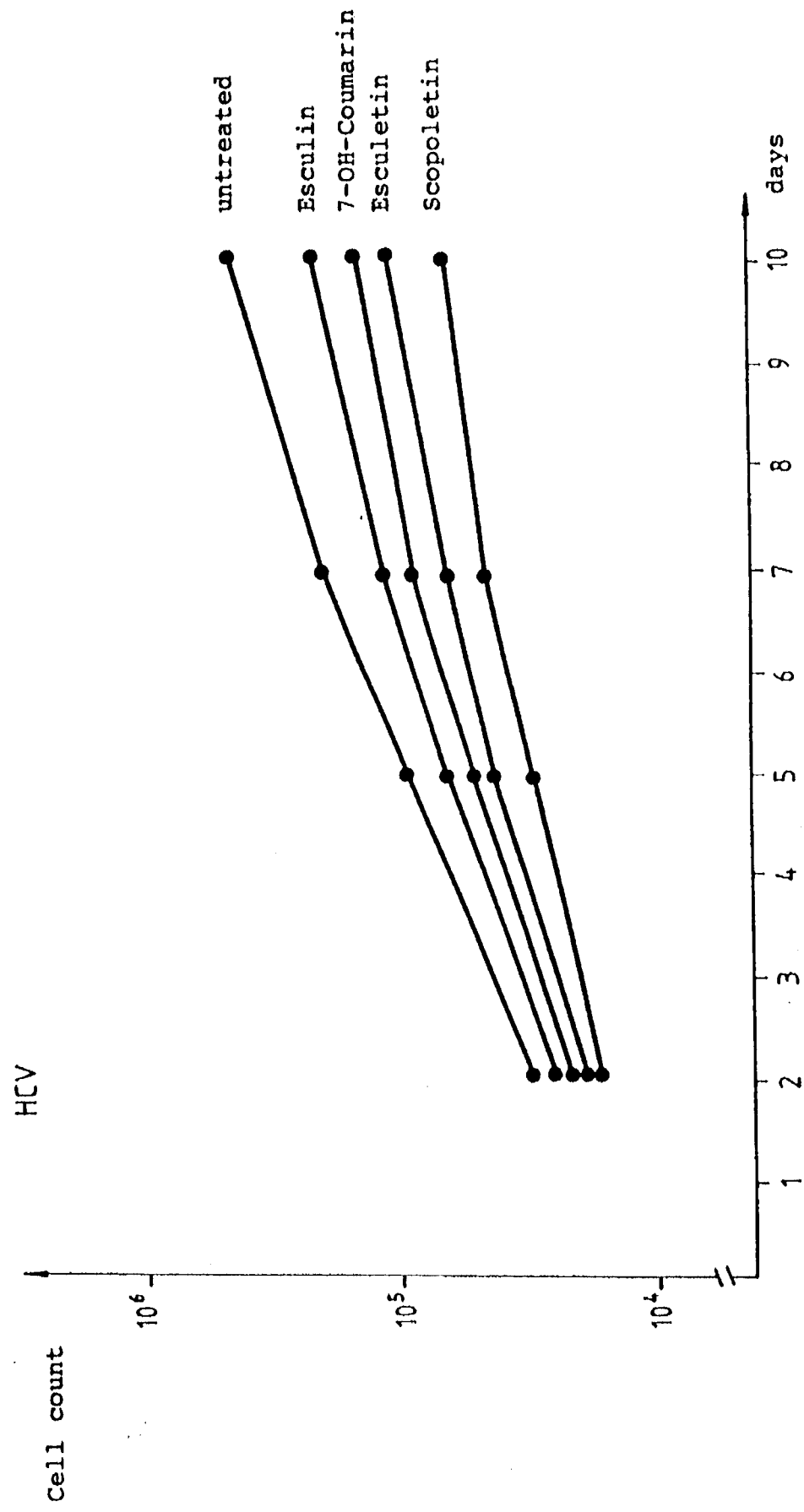
Figure 19:
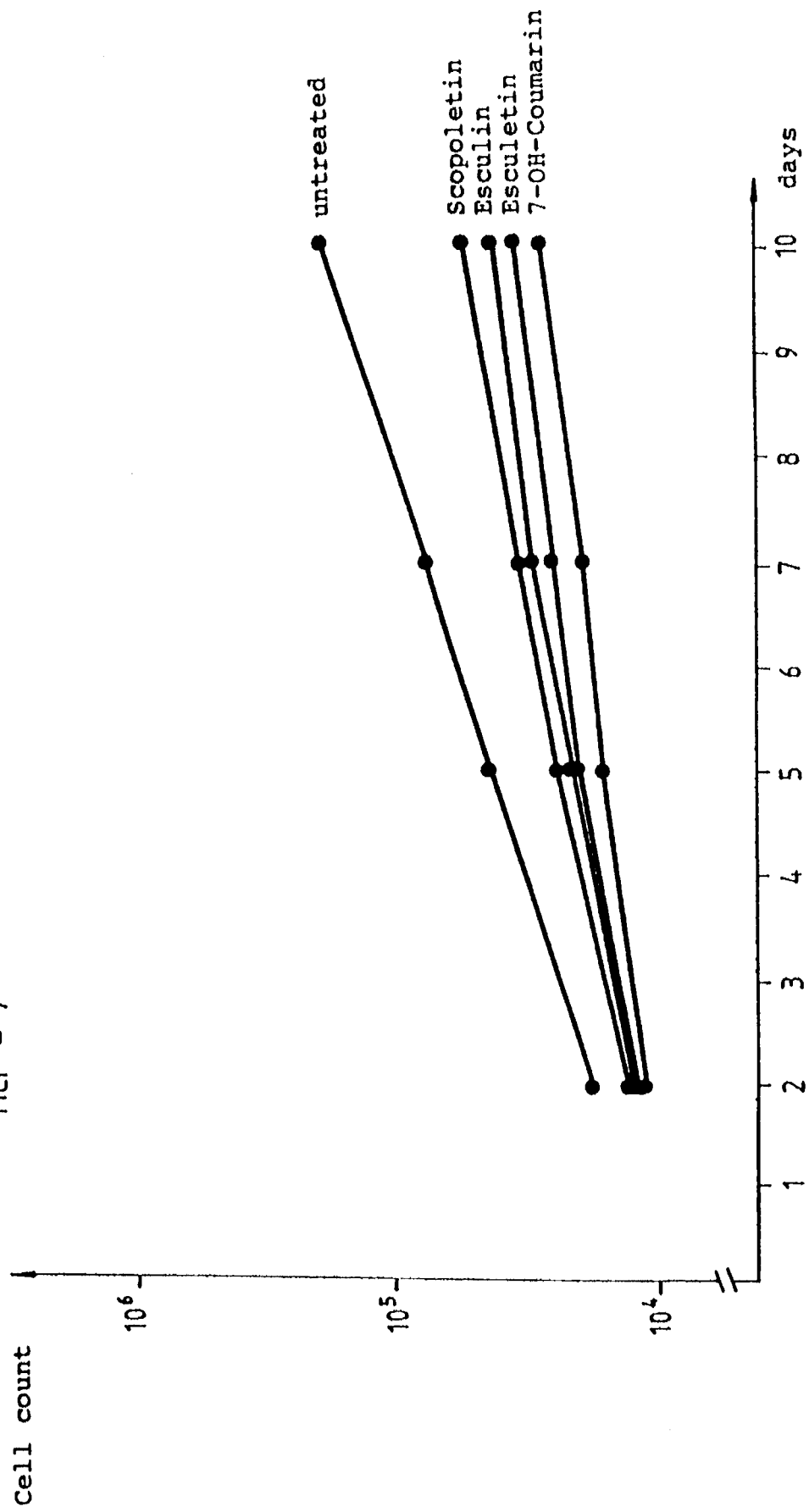
Figure 20:
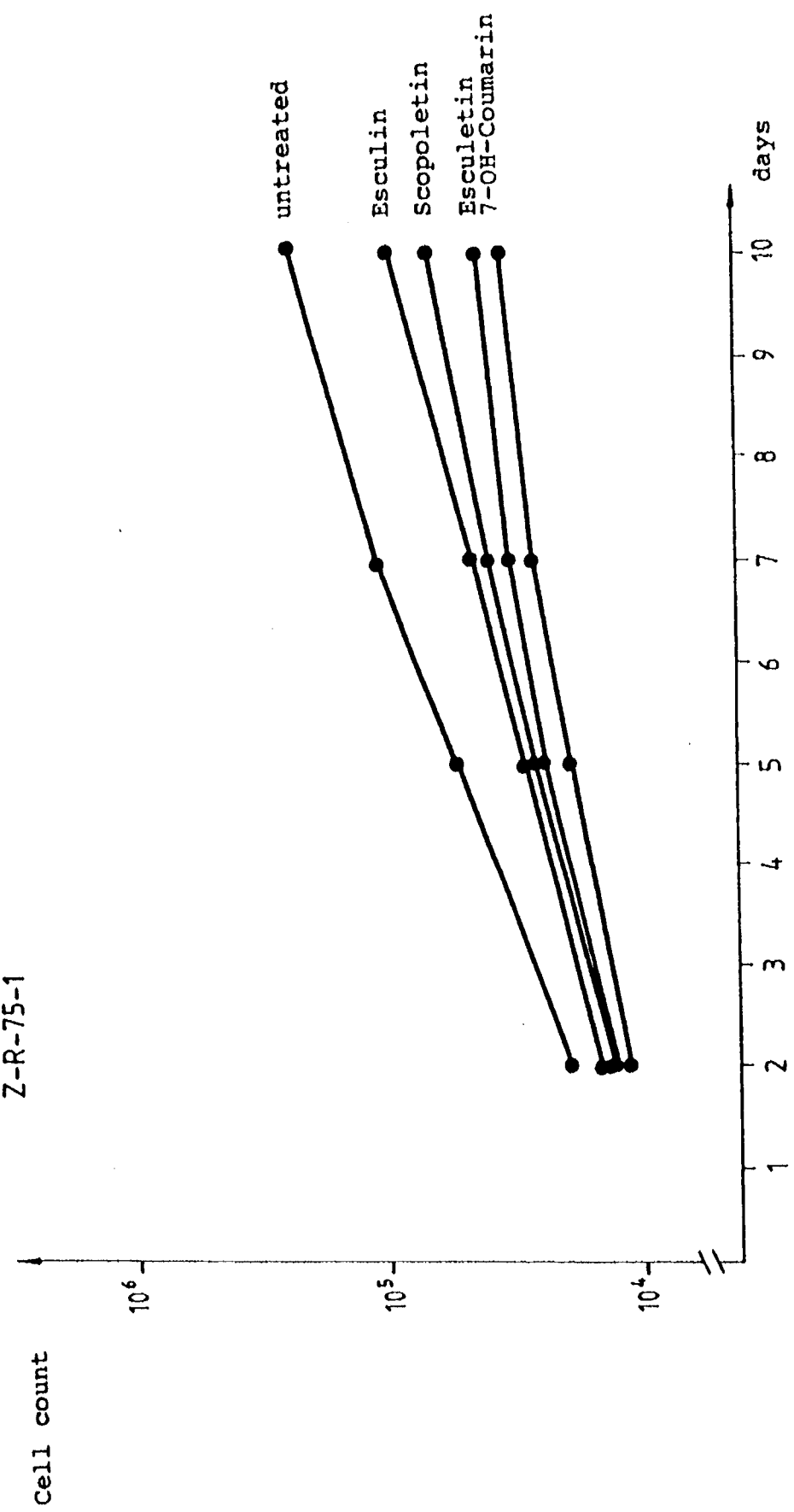
Figure 21:
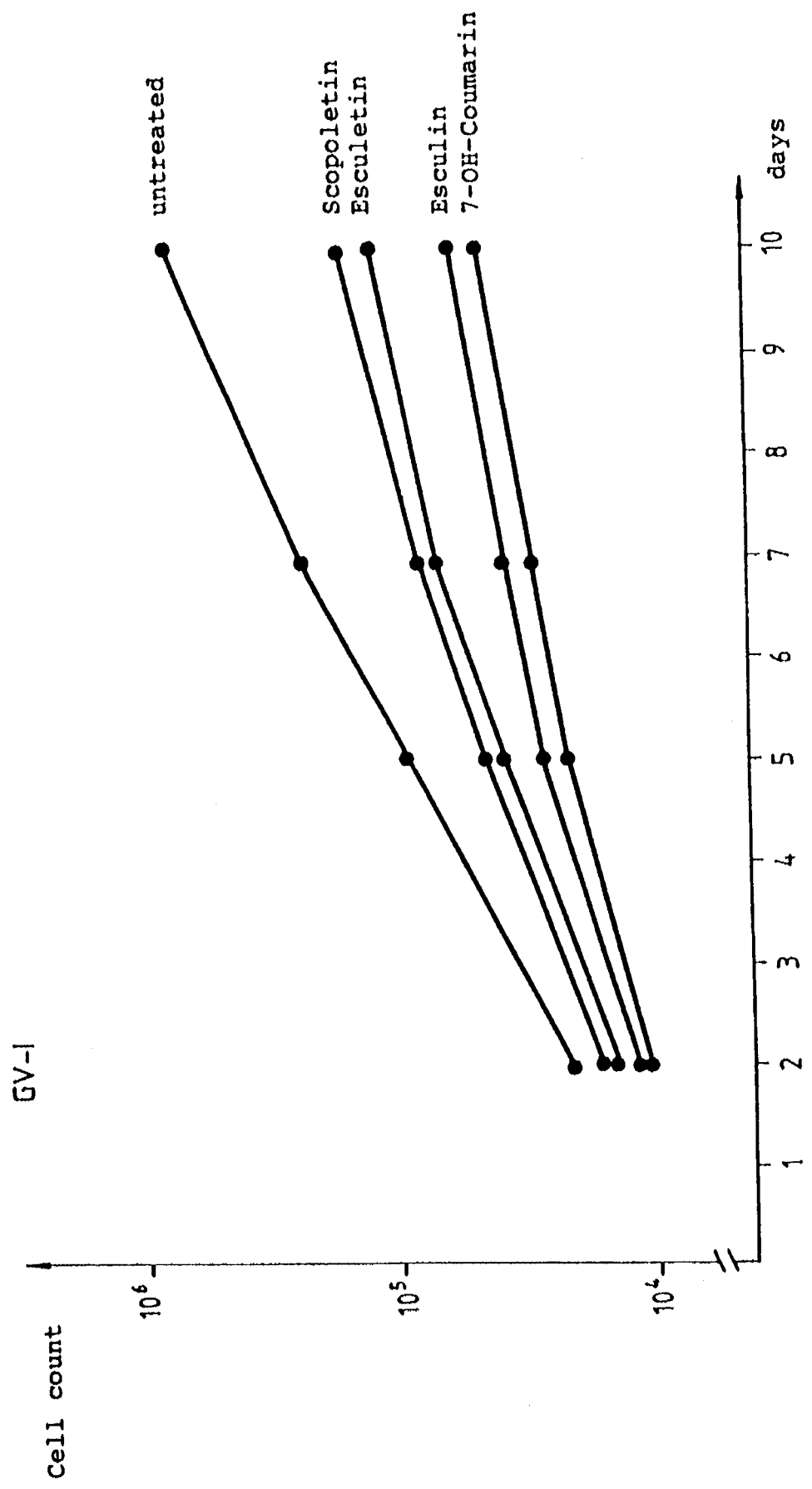
Figure 22:
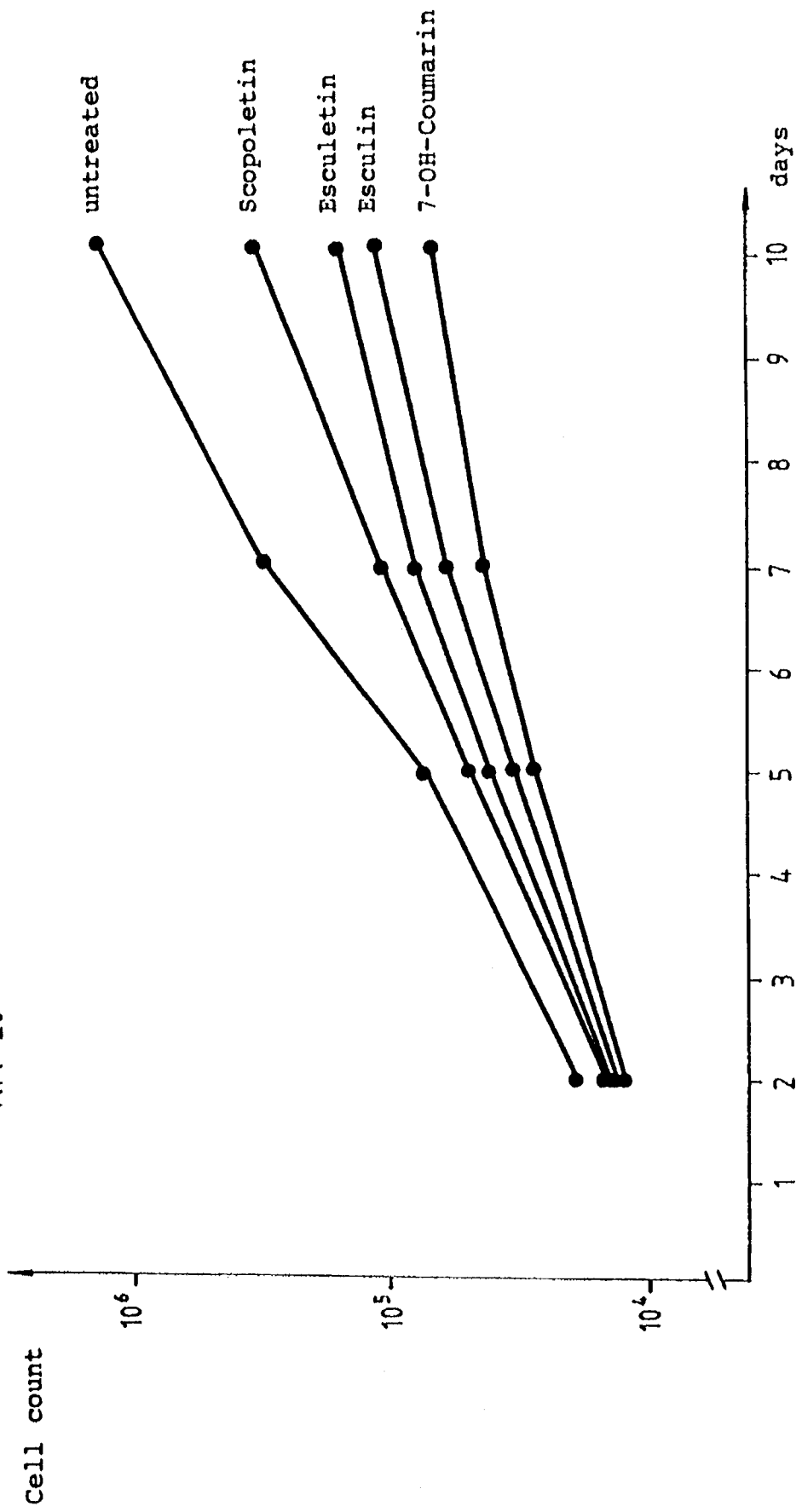
Figure 23:
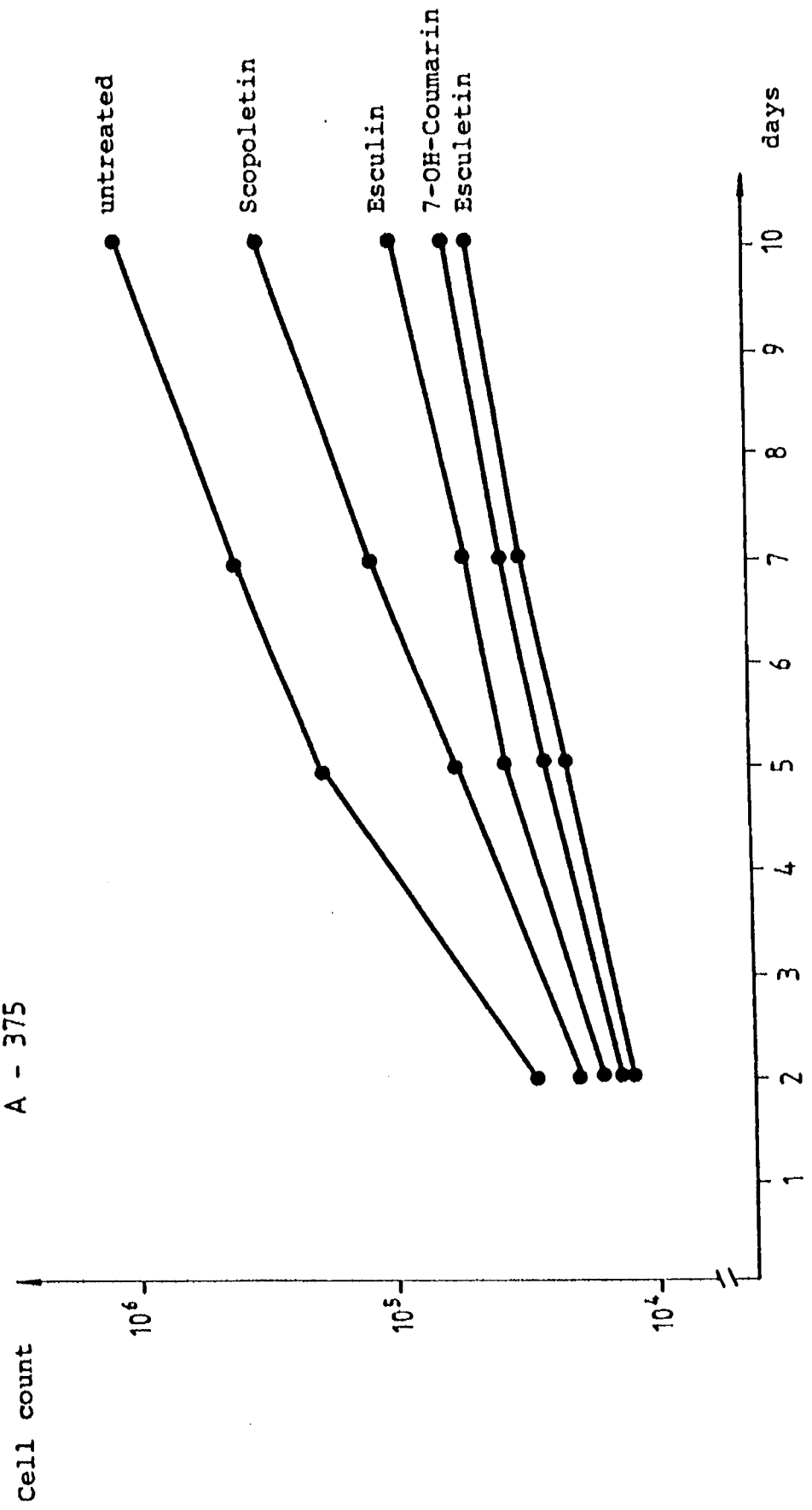
Figure 24:
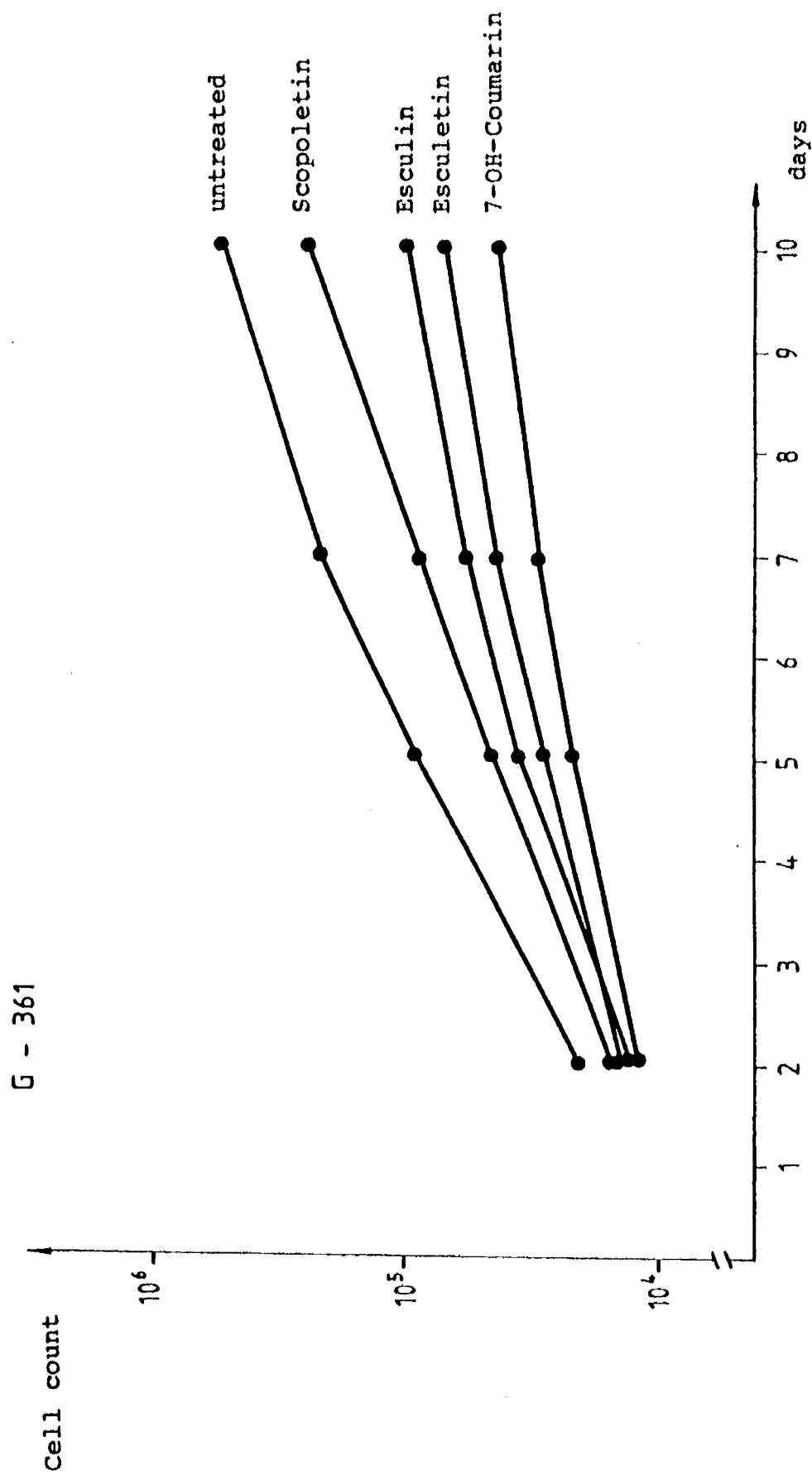

Cell growth was determined in the presence of 250 or 500 µM 7-OH-1,2-BP/ml medium combined with 20 nM testosterone per hole. The results are given in FIG. 9. They show that in the presence of 500 µM 7-OH-1,2-BP a virtually complete inhibition of cell growth is achieved. Further, the comparison with the compound 3-OH-1,2-BP proves that the latter is essentially ineffective.

EXAMPLE 9

Toxicity of 7-OH-1,2-BP in human beings 60 patients who were suffering from different, malignant tumors were treated with 7-OH-1,2-BP in a tolerance study. The initial dosage was 50 mg of the substance/day and the dosage was continuously increased up to 2000 mg/day. Over 8 consecutive weeks the patients were examined once a week for signs of systemic toxicity and organic dysfunctions. Because no side-effects at all had occurred at the end of the eighth week, the study was continued accompanied by the usual laboratory chemical controls and the daily dosage stepwise increased to 7000 mg/day. Toxic side-effects were not observed even with long-term administration of a daily dosage of 7000 mg/day.

EXAMPLE 10

Immunomodulating effect of 7-OH-1,2-BP

The influence of 7-OH-1,2-BP on the release of lymphokines by human mononuclear cells (MNC) was investigated by incubating the cells for 48 hours with various concentrations (cf. FIGS. 5 and 6) of 7-OH-1,2-BP dissolved in methanol for 48 hours. The stock solution contained 10 mg 7-OH-1,2-BP/ml methanol and was set with RPMI 1640 to the desired concentration in each case. The cells were isolated from the peripheral blood of healthy donors by density-gradient centrifugation according to the method described by Boyum in Scand. J. Clin. Lab. Invest. 21, 77 (1968) and, after washing three times with physiologic salt solution, was suspended in RPMI with a content of 100 M/ml penicillin, 100 μg/ml streptomycin and 2 mM glutamine (full medium). The lymphokines interleukin-1 (IL 1) and interleukin-6 (IL 6) were measured in the known manner in-vivo following induction with phytohemagglutinin (PHA), concanavalin A (ConA), lipopolysaccharide (LPS) or OKT 3 and adding increasing dosage amounts of 7-OH-1,2-BP. Measurement was carried out in an ELISA using microtiter plates as solid phase (fixed monoclonal antibodies against the lymphokine in question, polyclonal rabbit antibodies against the bound lymphokine, rabbit anti-IgG coupled to alkaline phosphatase as marker and p-nitrophenylphosphate as substrate).

The results are given in FIGS. 5 and 6.

They show that the release of IL 1 and IL 6, after stimulation with 7-OH-1,2-BP, was increased in the dosage range of 3.6 to 33 μg/ml. (The inhibition in the higher dosage range is based on the cytotoxic effect of the methanol used as solvent.) At low concentrations, the active substance accordingly stimulates the release of immunomodulators and therefore has a direct immunomodulation effect.

Further, the interaction among various cytokines after stimulation of MNC with 7-OH-1,2-BP (10 μg/ml) and LPS (10 to 10 to 100 pg/ml) was investigated on the MNC of 19 donors. In 6 out of 19 cases (32%) a co-stimulation of TNF-alpha, Il-1 and Il-6 was demonstrated. The calculation of the Spearman correlation coefficient showed a significant correlation between each of the three cytokines (Il-1-beta:Il-6 p=0,022, Il-1-beta:TNF-alpha p =0,007, Il-6:TNF-alpha p =0.007).

The results are shown graphically in FIG. 7.

EXAMPLE 11

Chemopreventive properties of 7-OH-1,2-BP

The chemopreventive properties of 7-OH-1,2-BP were tested on transgenic mice of the Onco Mouse™ type (mammary glands-neoplasms):

The extent to which 7-OH-1,2-BP is in the position to prevent or delay tumor occurrence and to increase the survival time of the animals was investigated. 7-OH-1,2-BP was fed in drinking water in concentrations of 200 μM/ml.

The results are given in table 6 below.

TABLE 6

Chemoprevention of 7-OH-1,2-BP as demonstrated on transgenic mice

| No. of mice without 7-OH-coumarin | No. of mice with 7-OH-1,2-BP | Tumor incidence % | |
|---|---|---|---|
| 28 | — | 9/28 | 32 |
| — | 38 | 3/38 | 8 |

EXAMPLE 12

Growth inhibition of "c-myc"-expressing tumor cells by 7-OH-1,2-BP a) DUKX cells (ovarian carcinoma cells from Chinese hamsters) which over-express "c-myc" products, were cultivated according to standard conditions, two comparative groups being grown. One group contained the medium 100 μg/ml 7-OH-1,2-BP, whilst the second group was cultivated as a control group without the active substance.

The development of the cultures was photographically recorded after 24, 48 and 72 hours; the results are given in FIG. 10. They show the dramatic inhibition of cell growth in the presence of 7-OH-1,2-BP (FIG. 10, $b_1$, to $b_3$).

b) The investigations as per a) were repeated, with the difference that the cells cultivated in the presence of 7-OH-1,2-BP were freed of the active substance after 24 hours, treated with trypsin and freshly inoculated, and the cell growth was photographically recorded after a further 48 hours in 7-OH-1,2-BP-free medium.

For comparison, corresponding cultures were cultivated for 24 hours with 7-OH-1,2-BP, treated with trypsin and freshly inoculated in a 7-OH-1,2-BP-containing medium.

Cell growth was likewise photographically recorded after 48 hours.

The results are given in FIG. 11.

They show a considerable cell growth of those cultures from which the 7-OH-1,2-BP was removed after 24 hours and not replaced during the consequent cultivation period (cf. FIG. $11b_1$). By comparison, cell growth was virtually completely inhibited in those cultures for which the second cultivation period also took place in the presence of 7-OH-1,2-BP (FIG. $11b_2$).

The results suggest that the permanent availability of the active substance 7-OH-1,2-BP is necessary for growth-inhibition of tumor cells with oncogenic overexpression.

We claim:

1. A method of treating susceptible human malignant tumors sensitive to 7-hydroxy-1,2-benzopyrone comprising administering to a person having same an effective amount of 7-hydroxy-1,2-benzopyrone.

2. The method according to claim 1 wherein the daily dose administered is 300 to 6000 mg.

3. The method according to claim 1 wherein the tumor treated is a brain tumor.

4. The method according to claim 1 wherein the tumor treated is renal carcinoma, prostatic carcinoma, cutaneous carcinoma, lung carcinoma or leukemia.

5. The method according to claim 1 wherein the tumor treated is an oncogenetically induced tumor.

6. The method according to claim 1 wherein the tumor is hormone dependent and hormones are also administered to the patient.

* * * * *